(12) United States Patent
Gagnon et al.

(10) Patent No.: US 10,099,400 B2
(45) Date of Patent: Oct. 16, 2018

(54) METHOD AND SYSTEM FOR DETECTING THE QUALITY OF DEBARKING AT THE SURFACE OF A WOODEN LOG

(75) Inventors: Richard Gagnon, Quebec (CA); Jean-Pierre Couturier, Quebec (CA); Philippe Gagné, St-Nicolas (CA); Feng Ding, Quebec (CA); Fadi Ibrahim, Edmondton (CA)

(73) Assignee: CENTRE DE RECHERCHE INDUSTRIELLE DU QUÉBEC, Québec (CA)

( * ) Notice: Subject to any disclaimer, the term of this patent is extended or adjusted under 35 U.S.C. 154(b) by 1375 days.

(21) Appl. No.: 13/614,761

(22) Filed: Sep. 13, 2012

(65) Prior Publication Data
US 2013/0333805 A1 Dec. 19, 2013

(30) Foreign Application Priority Data
Jun. 19, 2012 (CA) .................................... 2780202

(51) Int. Cl.
*G06K 9/00* (2006.01)
*B27L 1/00* (2006.01)
(Continued)

(52) U.S. Cl.
CPC .................. *B27L 1/00* (2013.01); *B27L 1/08* (2013.01); *G01N 21/8986* (2013.01)

(58) Field of Classification Search
CPC .......... Y10T 428/31982; G01B 11/245; G01B 11/2522; G06T 7/0057
See application file for complete search history.

(56) References Cited

U.S. PATENT DOCUMENTS

| 2,769,468 A | 11/1956 | Swanson |
| 3,554,249 A | 1/1971 | Arnelo |

(Continued)

FOREIGN PATENT DOCUMENTS

| WO | 91007653 A1 | 5/1991 |
| WO | 2010037206 A1 | 4/2010 |

OTHER PUBLICATIONS

Spurr et al, Forest Inventory; The Ronald Press Company, NY, p. 476, 1952.
(Continued)

*Primary Examiner* — Vu Le
*Assistant Examiner* — Guillermo Rivera-Martinez

(57) ABSTRACT

A method and system for detecting and controlling the quality of debarking at the surface of a wooden log provide information on main parameters related to the debarking quality of the log surface, including fiber loss and residual bark. The debarking quality detecting method and system involve measurement of three-dimensional profile of at least a portion of the log surface to generate corresponding profile image data, which is processed to generate data indicative of the texture of the log surface. The texture data is then analyzed to generate resulting data on the debarking quality parameters. That quality indicative information can be generated on a continuous basis to provide an objective assessment of the quality performance in real-time in view of target productivity, and may then be used to perform optimal adjustments of the debarker operating parameters, either manually by the operator or automatically through feedback control.

32 Claims, 25 Drawing Sheets

(51) Int. Cl.
*B27L 1/08* (2006.01)
*G01N 21/898* (2006.01)

(56) References Cited

U.S. PATENT DOCUMENTS

| | | | |
|---|---|---|---|
| 4,185,672 | A | 1/1980 | Vit |
| 4,188,544 | A | 2/1980 | Chasson |
| 4,399,849 | A | 8/1983 | Nowakowski |
| 4,514,816 | A | 4/1985 | Ollus |
| 4,831,545 | A | 5/1989 | Floyd |
| 4,916,629 | A | 4/1990 | Bogue |
| 4,992,949 | A | 2/1991 | Arden |
| 5,247,978 | A | 9/1993 | Silenius |
| 5,274,244 | A | 12/1993 | Johansson |
| 5,335,790 | A | 8/1994 | Geiger |
| 5,815,198 | A | 9/1998 | Vachtsevanos |
| 5,884,775 | A | 3/1999 | Campbell |
| 5,949,086 | A | 9/1999 | Reponen |
| 6,060,677 | A | 5/2000 | Ulrichsen |
| 6,064,478 | A | 5/2000 | Paul |
| 6,087,608 | A | 7/2000 | Schlichter |
| 6,137,894 | A | 10/2000 | Ahonen |
| 6,166,393 | A | 12/2000 | Paul |
| 6,252,189 | B1 | 6/2001 | Campbell |
| 6,493,076 | B1 | 12/2002 | Laitinen |
| 6,526,154 | B1 * | 2/2003 | Taipale ............... B27L 1/00 382/100 |
| 6,539,993 | B1 | 4/2003 | Starr |
| 6,546,979 | B2 | 4/2003 | Jonkka |
| 6,614,041 | B1 | 9/2003 | Lappalainen |
| 6,936,834 | B2 | 8/2005 | Henry |
| 6,991,011 | B2 | 1/2006 | Huhtasalo |
| 2004/0246473 | A1 * | 12/2004 | Hermary ........... G01B 11/245 356/237.1 |
| 2005/0072494 | A1 * | 4/2005 | Price ................ G05B 15/02 144/340 |
| 2006/0272745 | A1 * | 12/2006 | Niinimaki ........... B27L 1/025 144/340 |
| 2007/0286474 | A1 | 12/2007 | Dralle |
| 2010/0236664 | A1 * | 9/2010 | Brdicko ............... B27L 1/00 144/356 |
| 2010/0332438 | A1 * | 12/2010 | Toland ............. G06F 17/5009 706/52 |
| 2012/0227866 | A1 * | 9/2012 | Barker ............... B23Q 17/20 144/357 |

OTHER PUBLICATIONS

Philip, Measuring Trees and Forests, 2nd ed. CAB Inter., p. 310, Wallingford, Oxforchire, UK, 1994.
Wilhelmsson et al., Models for predicting wood properties in stems of Picea abies and Pinus sylvestris in Sweden, Scand. J. Forest Res.,pp. 330-350, 17, 2002.
Marshall et al, Effects of bark thickness estimates on optimal log merchandiding, Forest Products Journal, vol. 56, No. 11/12, 2006.
Baroth, Literature review of the latest development of wood debarking, Control Engineering Laboratory, University Oulu, p. 4, Report A No. 27, Aug. 2005.
Laganiere et al., Effects of radial force and tip path overlap on the ring debarking efficiency of frozen balsam fir logs, Forest Products Journal, vol. 55, No. 3, 2005.
Thomas, Automated detection of surface defects on barked hardwood logs and stems using 3-D laser scanned data, Virginia Polytechnic Institute and State University, Virginia, USA, Sep. 2006.

* cited by examiner

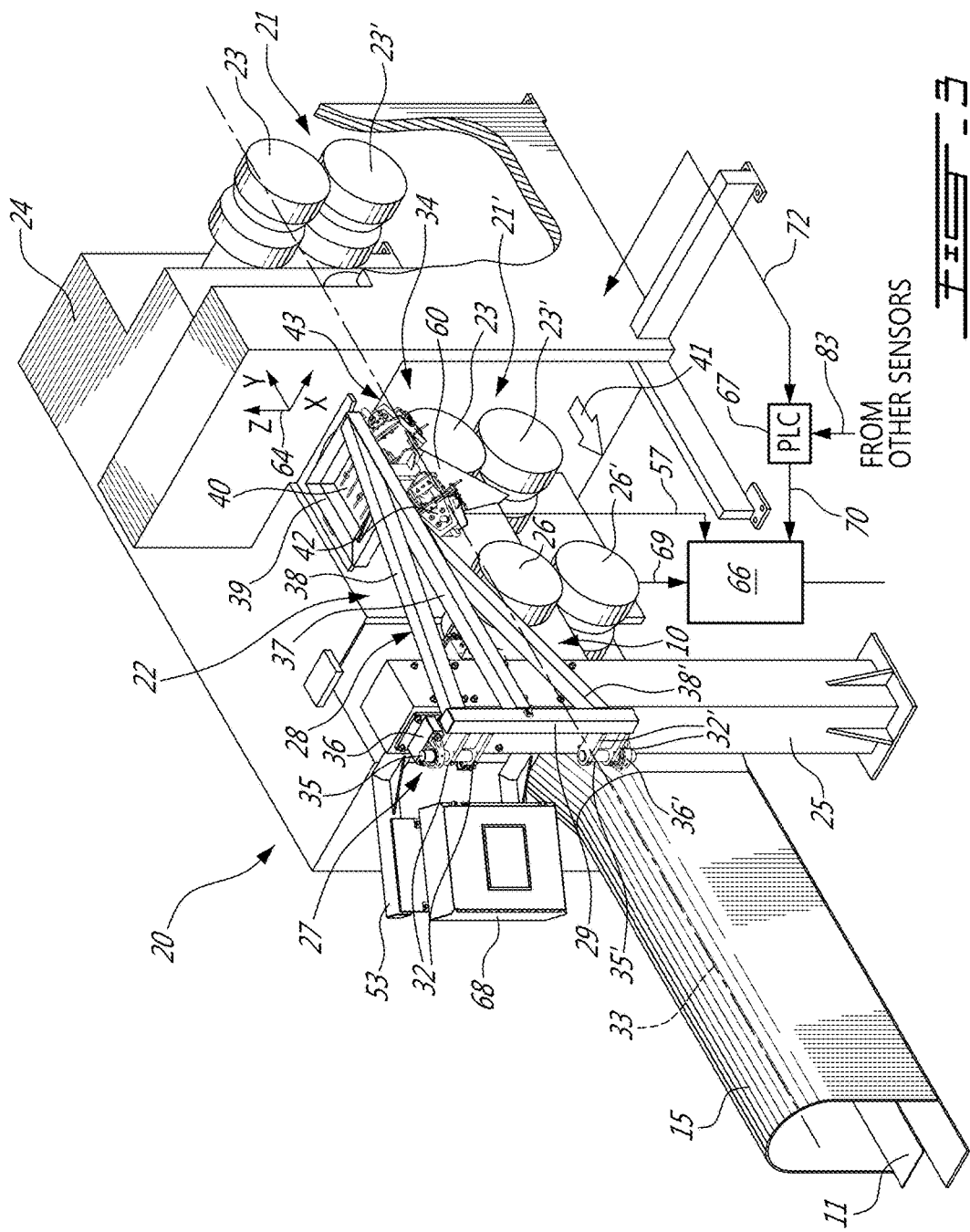

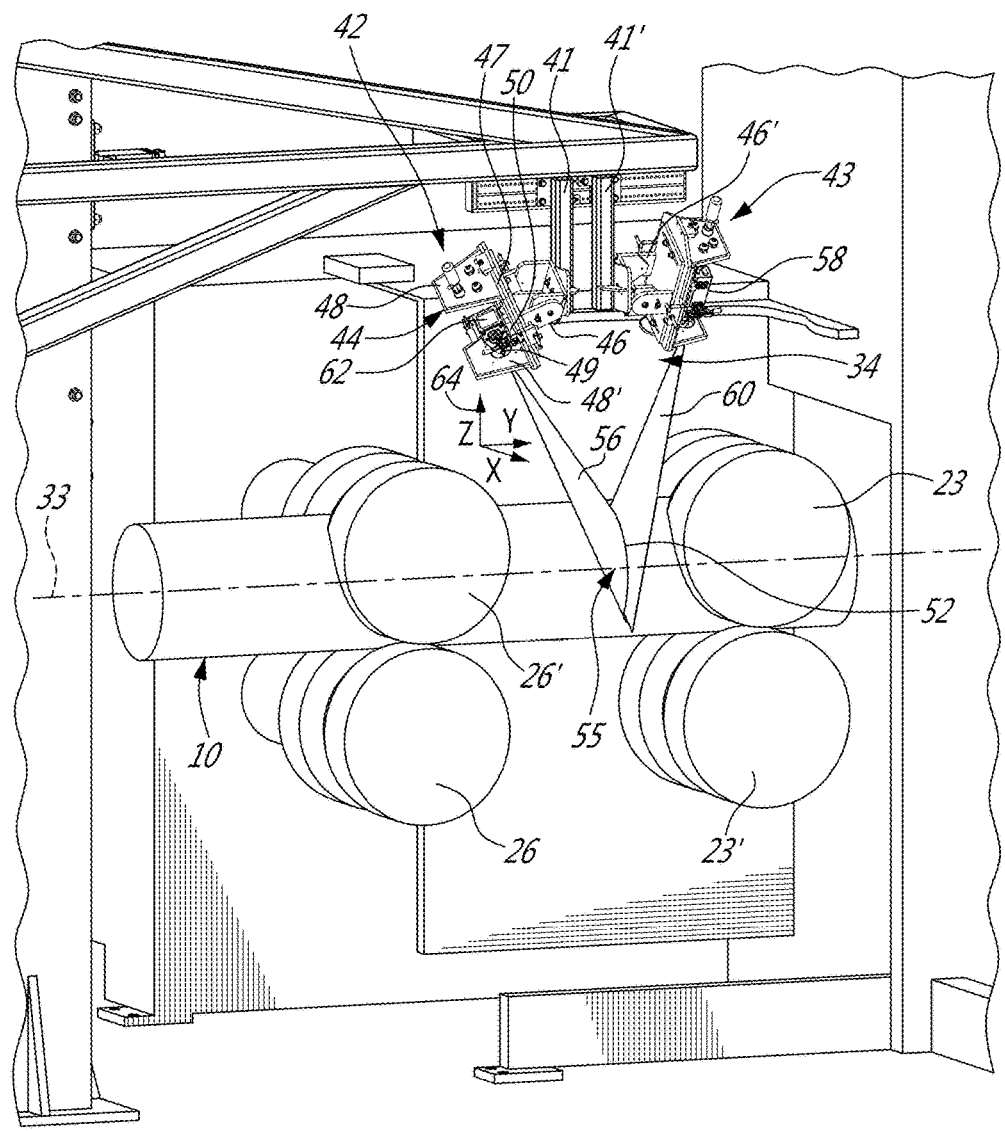

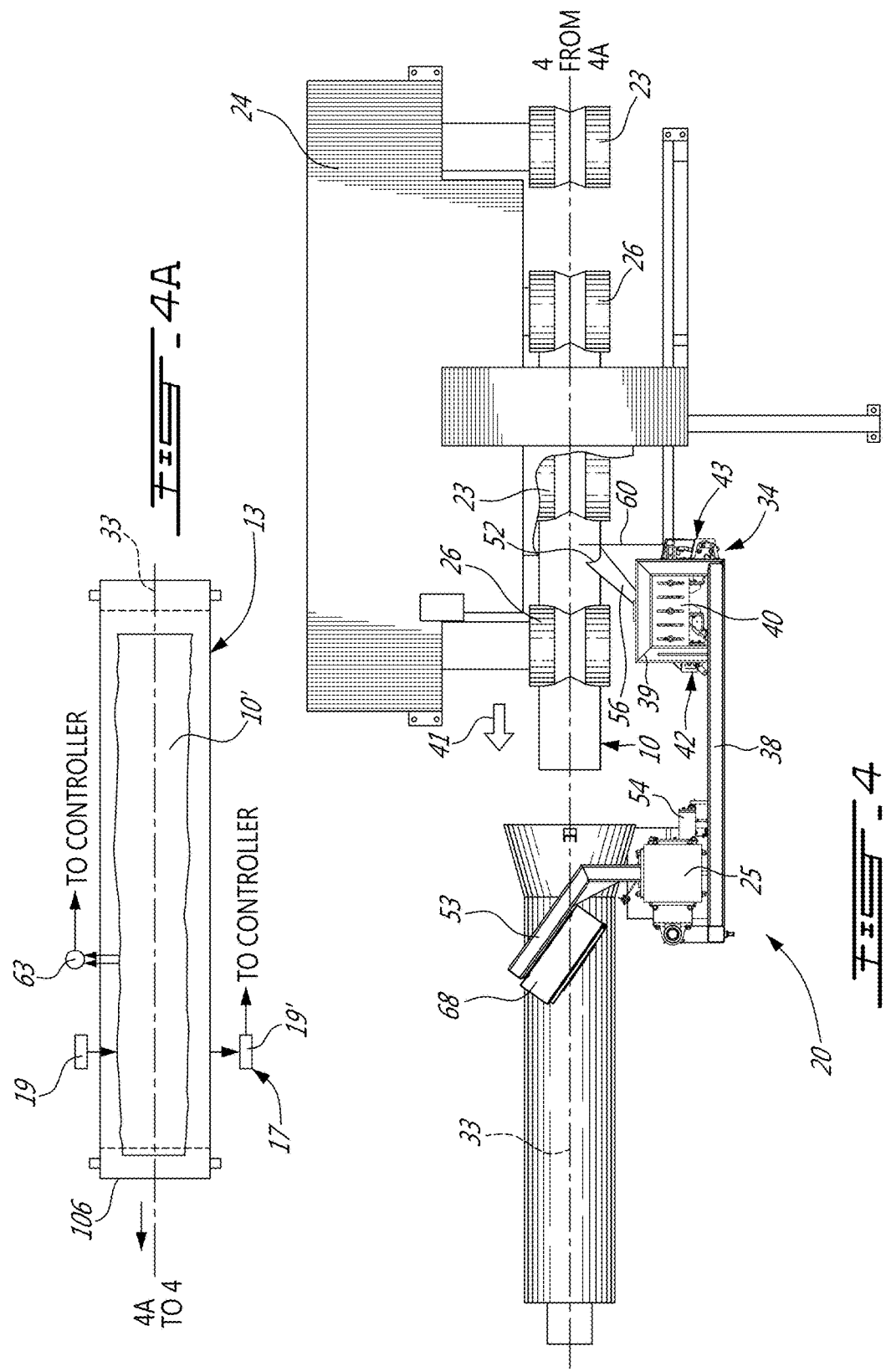

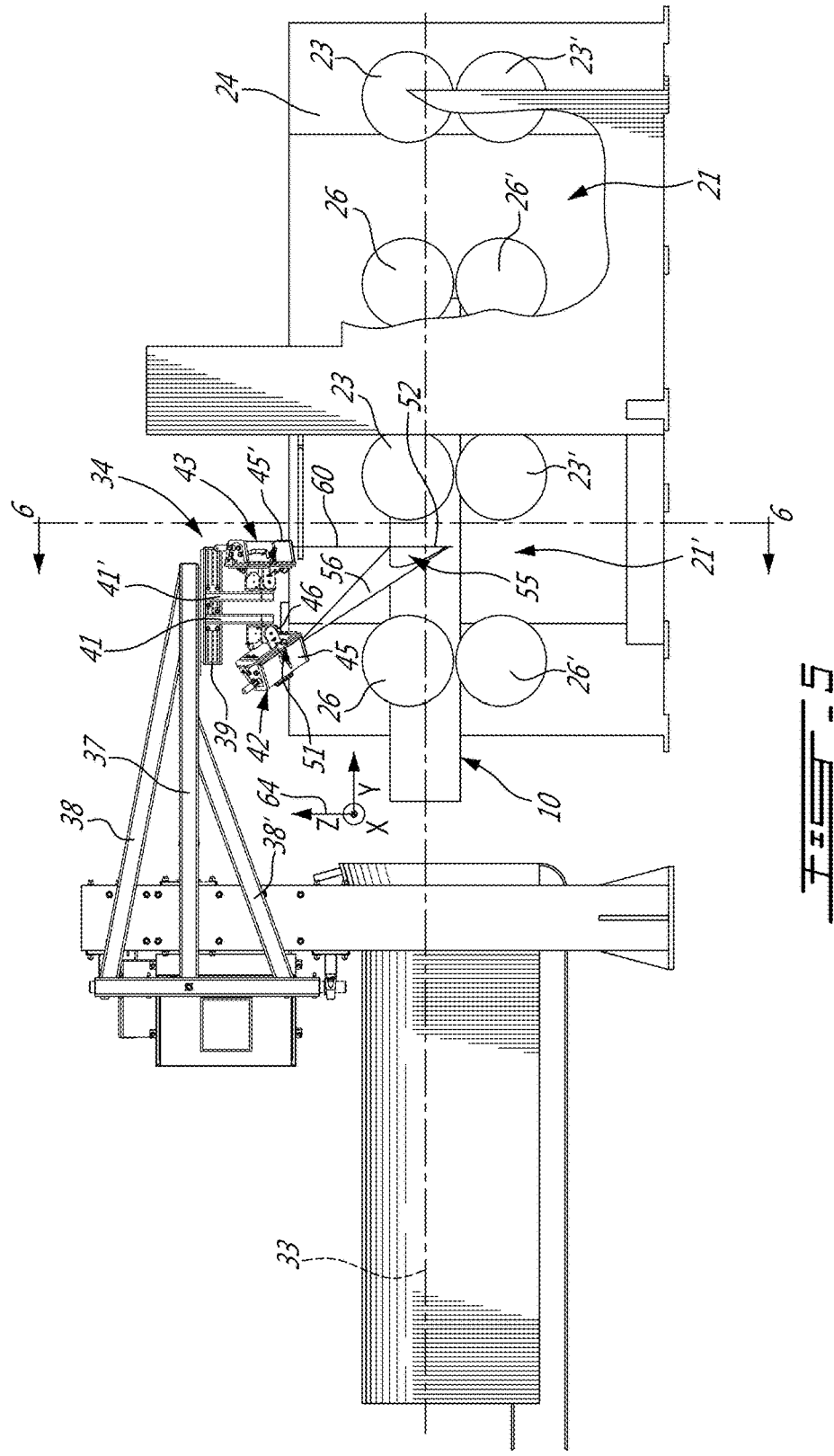

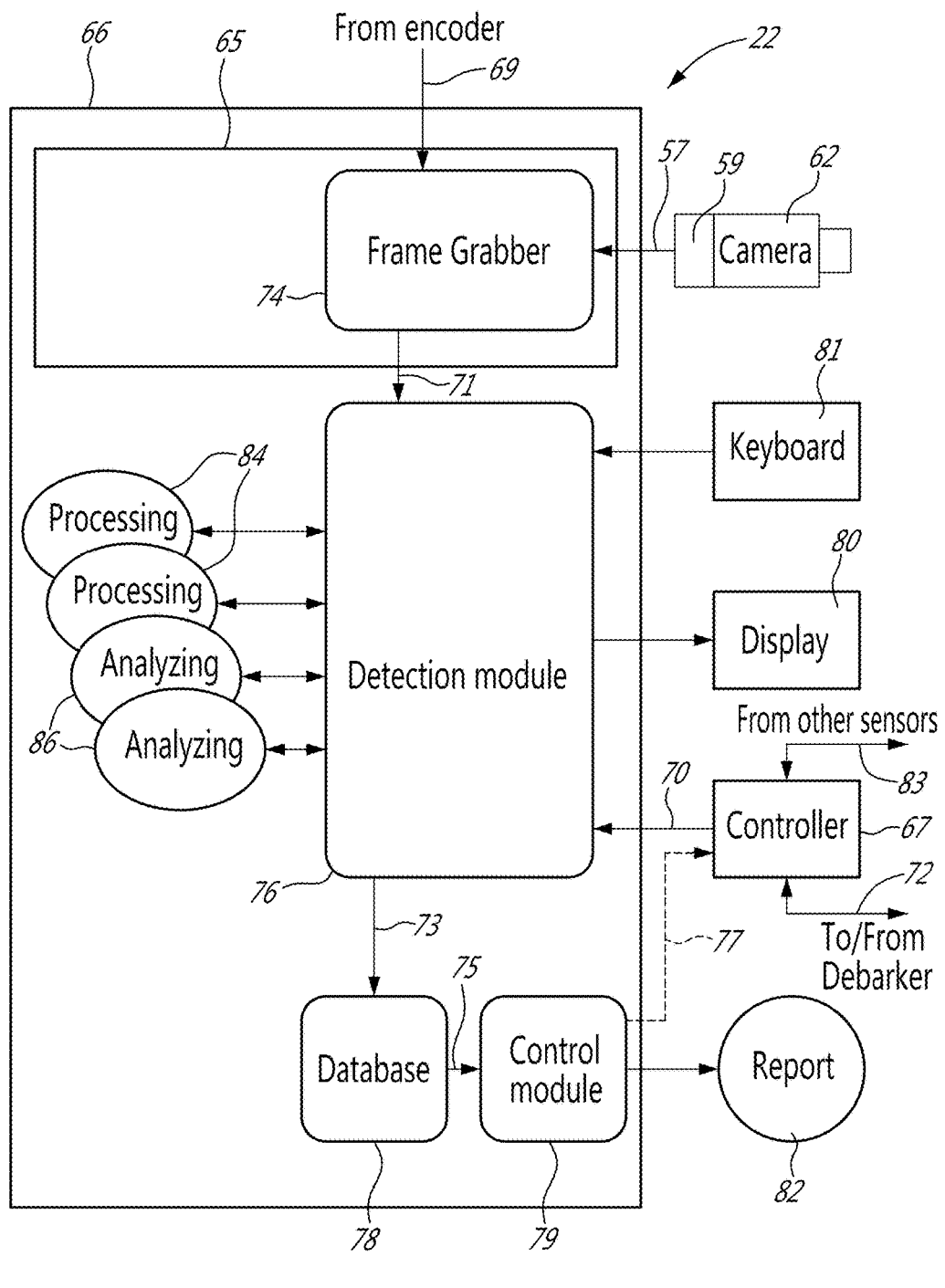

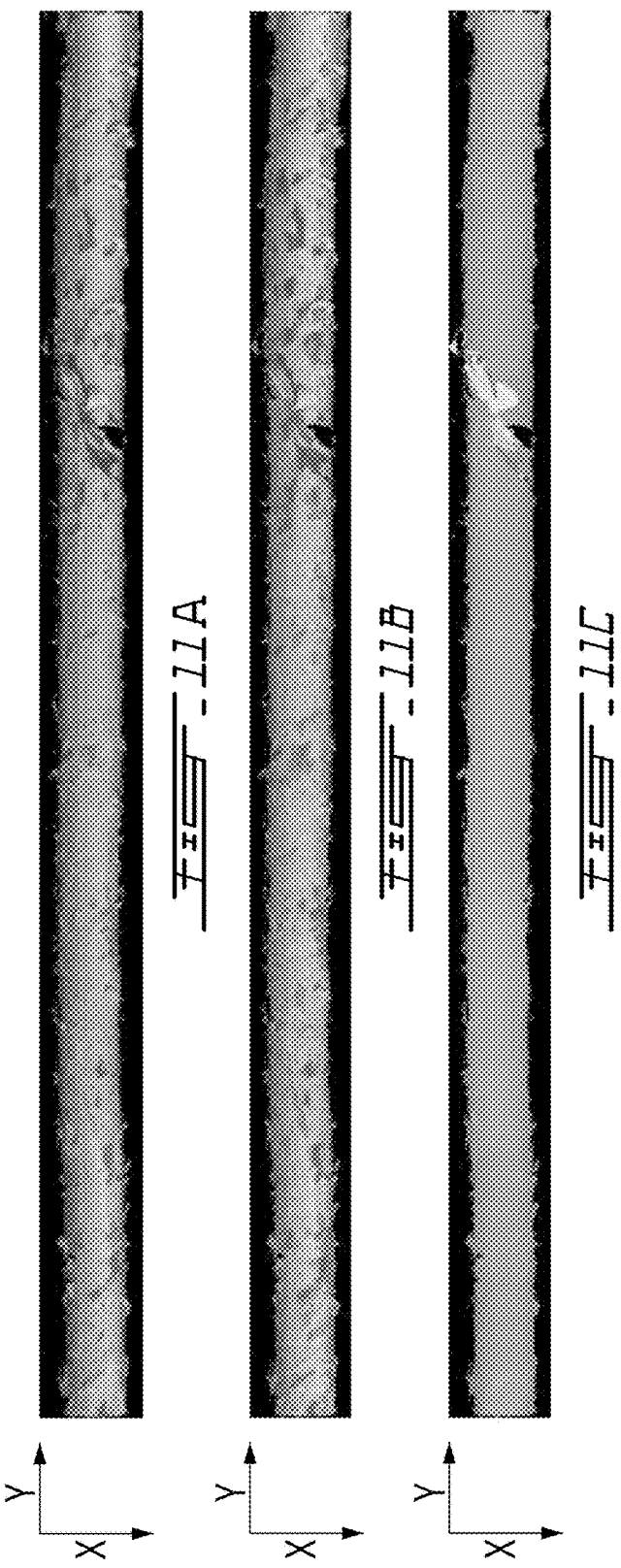

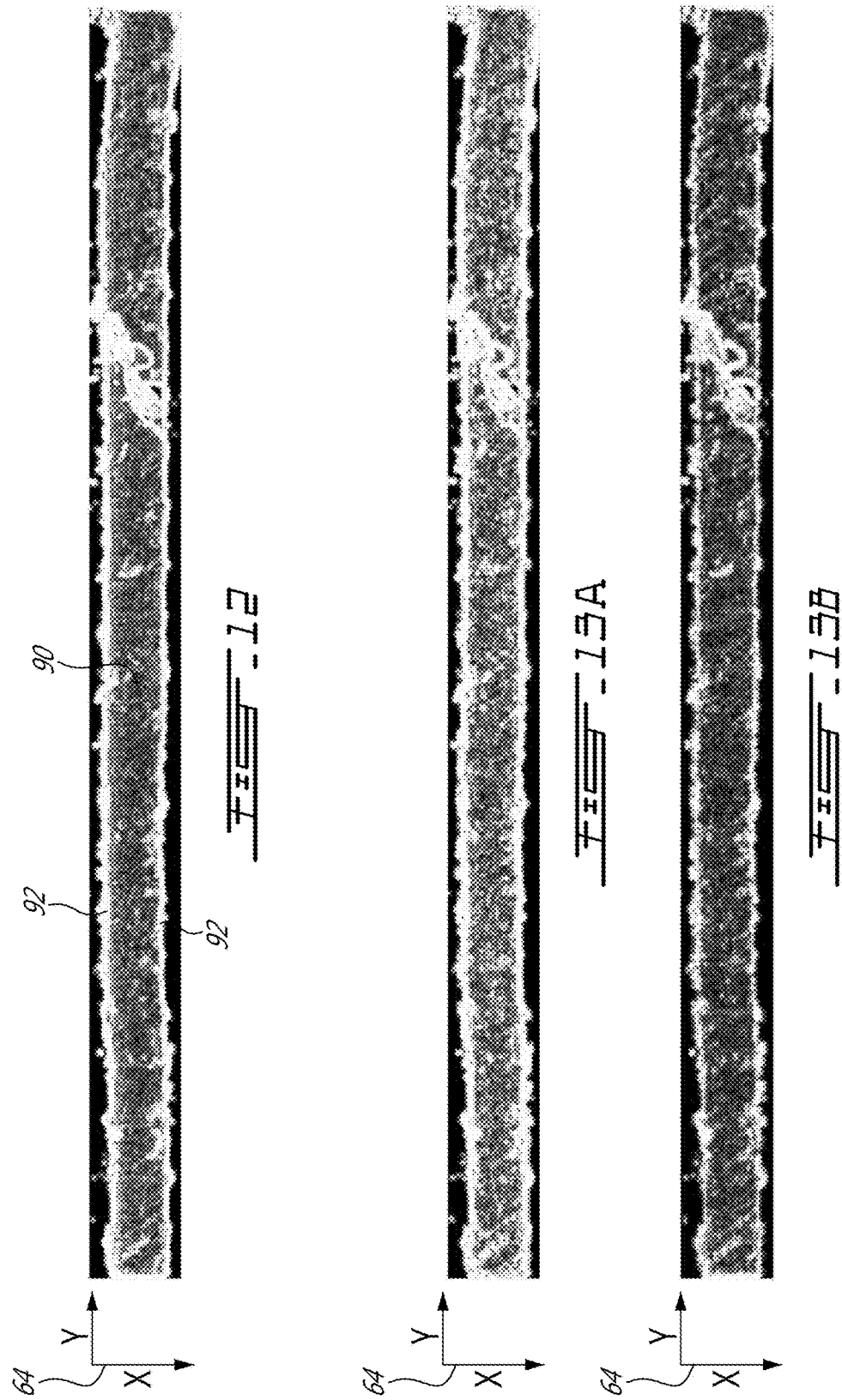

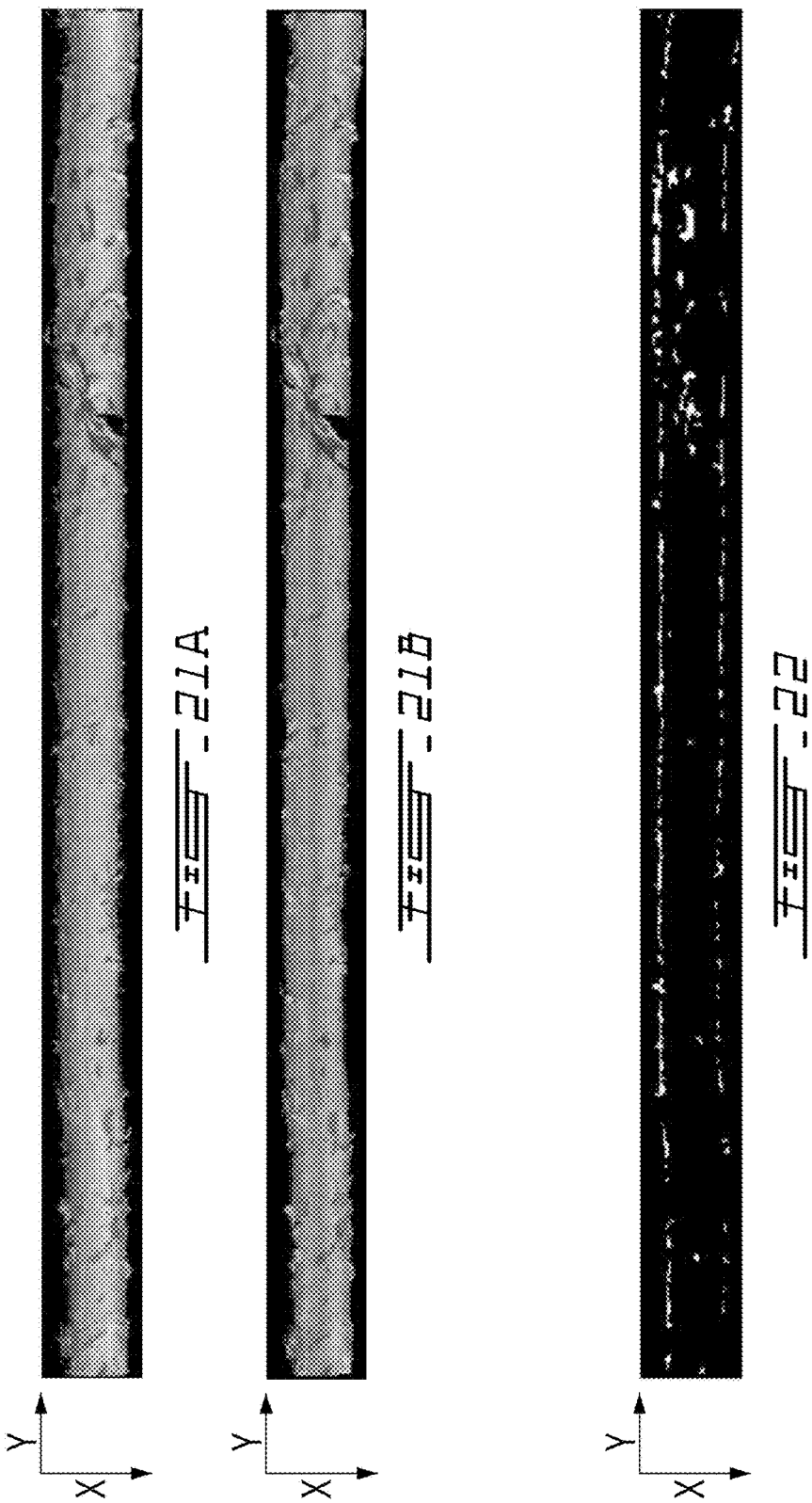

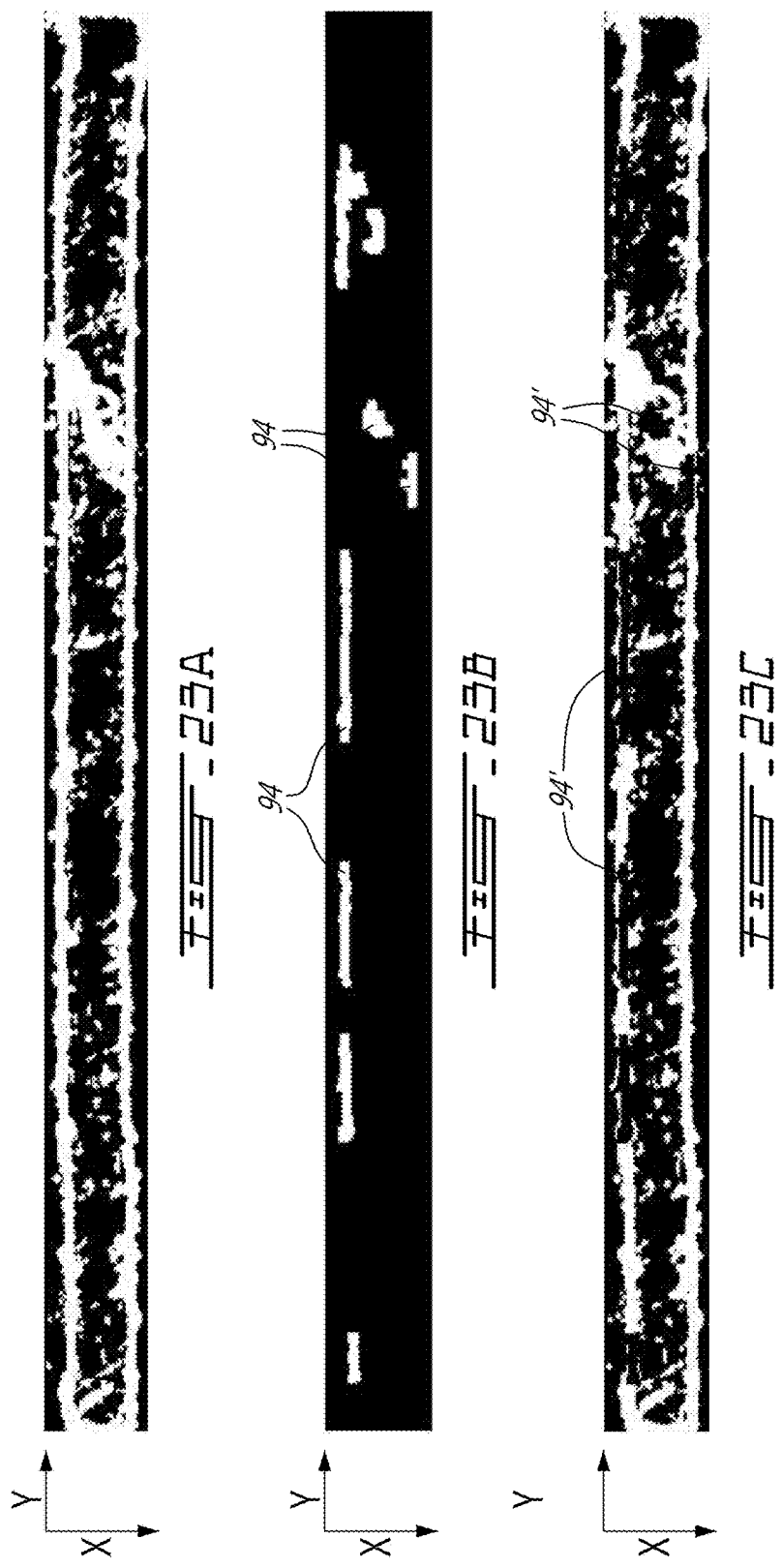

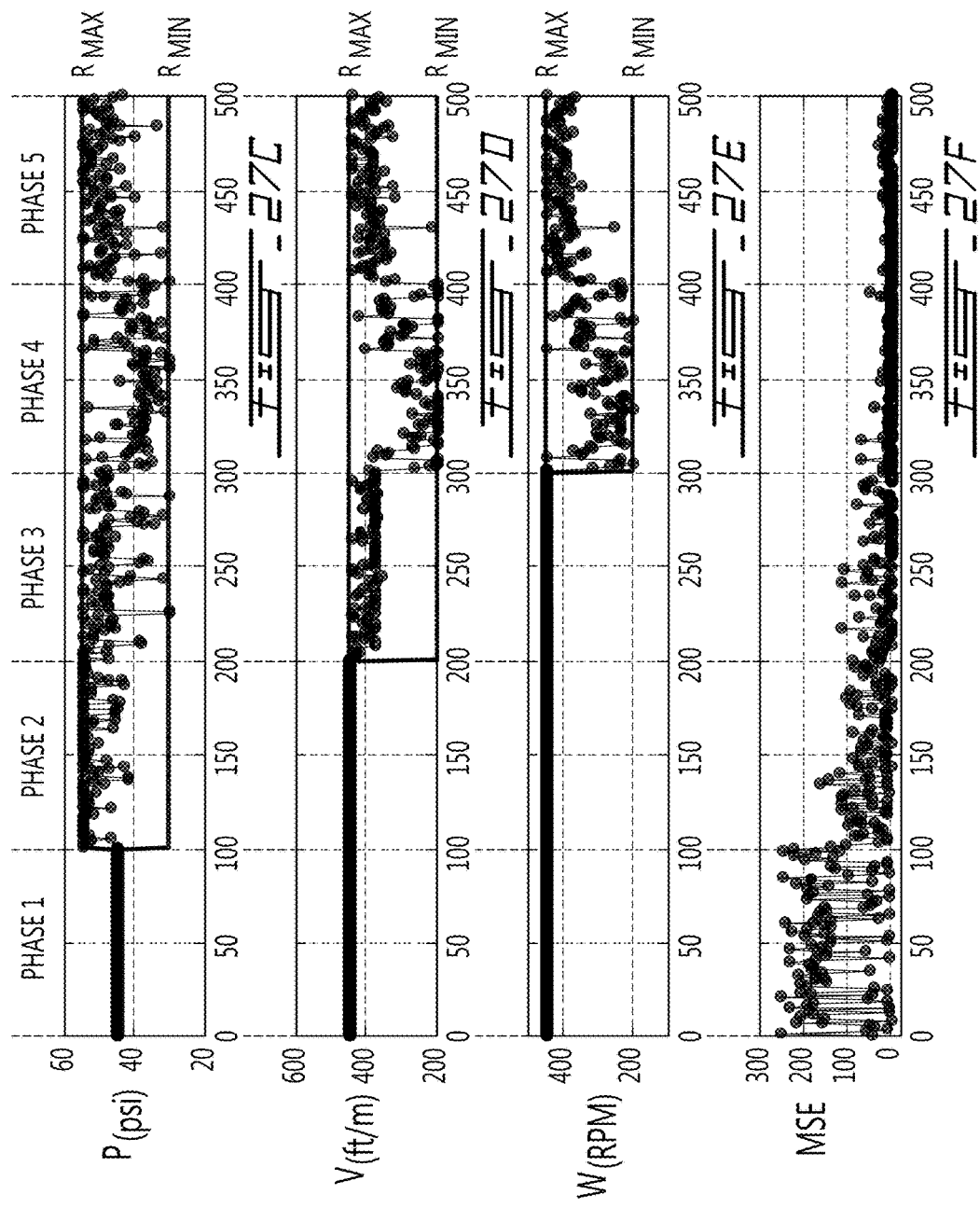

METHOD AND SYSTEM FOR DETECTING THE QUALITY OF DEBARKING AT THE SURFACE OF A WOODEN LOG

FIELD OF THE INVENTION

The present invention relates to the field of wood processing, and more particularly to methods and systems for detecting and controlling the quality of debarking performed on wooden logs in lumber mills.

BACKGROUND ART

The debarking process is a very important step for many industrial uses of wood from logs. Wood chips produced through the debarking process are the main raw materials of most pulp and paper, MDF and HDF boards industries. Bark has minimal value and may be associated with net financial loss incurred by the forest industry. Wood chips typically come from sawmills where they are produced from logs that have been debarked, and the debarking quality directly influences the chip quality and sawmill production yield. The debarking of wooden logs is an operation consisting of removing from the surface of each log a thin layer of material mainly containing bark (outer bark and inner bark) with some cambium, with the objective to preserve intact the fiber material under the cambium layer, so as to maximize economic yield obtained from lumber and wood chips. Typically, wood chips represent roughly 50% of the volume of material produced, within which a maximum of 1% (1.5% in winter) of bark content is targeted, while aiming at preserving the full potential of lumber yield for each piece of timber. Since bark remaining on chips deteriorates the pulp being produced, it is within the industry practices that buyers of wood chips such as pulp producers and pressed board manufacturers, to impose economic penalties to chips providers or even refuse delivery in cases where bark content limit is exceeded. In the other hand, the compliance with that requirement may involve fiber loss from log surface as a result of debarking, causing a loss of income, due to fiber material loss in wood chips associated with residual fiber in bark, as well as to the lower value of lumber production attributed to a lower quality associated with surface and dimensional defects. In other words, residual bark on the debarked log surface increases the percentage of bark content in the wood chips which may thus be downgraded or refused by the mills, while excessive debarking will result in fiber loss, thus decreasing sawmills revenues. The optimization of debarking process is very complex, mainly due to numerous variables to be considered in order to concurrently decrease fiber loss and residual bark on the debarked log surface. In practice, seeking to operate the debarking process at an optimal point is a difficult task. Generally, wood processing involves a large variation in raw material characteristics at the input end of the sawing process in contrast with upstream processes such as drying and planning. Therefore, debarking should be entirely efficient in terms of production capacity and debarked log quality while being fed in timber pieces of various diameters, moisture contents and wood species. The debarking equipment currently available includes the drum debarker, hydraulic debarker and rotary ring debarker, the two latter being used on sequential, respectively transverse and lengthwise, log processing lines, while the former is used for debarking logs in batches. During the past years, the rotary ring debarker has been the most used type of debarking equipment in sawmills. The rotary ring debarker makes use of spinning knifes mounted on a rotary ring as cutting tools, whose angular position as well as the magnitude of controlled pressure applied thereto are usually adjusted periodically to achieve an acceptable debarking quality taking into account a large variation at the input of the debarking process.

The variations of log physical properties, environmental and storage conditions, as well as debarking operating conditions strongly influence the residual bark and fiber loss levels on the surface of debarked logs. The performance of a rotary ring debarker depends on log characteristics such as wood species, moisture content, freshness, mean diameter, and bark thickness. In particular, different wood species have their own characteristics that may affect the debarking process, for example black spruce is more easily debarked than balsam fir during winter. Moisture content is the most important factor in wood/bark adhesion strength. As to freshness, lowest bark/wood shear strengths can be observed with fresher logs as compared to aged logs. As to diameter, it is generally observed that amongst the debarked logs of a processed batch, those of small diameter are often poorly debarked. It is also well known that bark thickness varies between wood species, parts of the tree, as well as harvesting areas, and thus influences the choice of debarking operating parameters, especially pressure applied to the tools, as reported by Spurr, S. H, et al. in "Forest Inventory" The Ronald Press Company, NY. 1952, pp. 476; Philip, M. S. in "Measuring Trees and Forests", $2^{nd}$ ed. CAB Inter., Wallingford, Oxfordshire, UK. 1994, pp. 310; Wilhelmsson, L., et al. in "Models for predicting wood properties in stems of *Picea abies* and *Pinus sylvestris* in Sweden", Scand. J. Forest Res. 17, 2002, pp. 330-350; and Marshall, H. D., et al. in "Effects of bark thickness estimates on optimal log merchandiding", Forest Products Journal Vol. 56, No. 11/12, 2006. As to the effects of environmental and storage conditions on debarking quality, air temperature, which influences temperature state of log surface (i.e. frozen or non-frozen), has an effect on wood/bark adhesion strength when the log moisture content is greater than fiber saturation point, as reported by Baroth, R., in "Literature review of the latest development of wood debarking", Control Engineering Laboratory, University Oulu, Report A No. 27, August 2005, p. 4. The storage conditions such as storage time, ambient air conditions (temperature, relative humidity, velocity) also influence moisture content distribution in logs, which results in variation of wood/bark adhesion strength finally giving rise to debarking quality. Finally, the performance of a rotary ring debarker depends on its main operating parameters, namely pressure applied to the cutting tools, log feed speed, ring rotational speed, and cutting tool tip overlap. It is known that a poorly maintained or misadjusted debarker may cause log surface damages and well as sections of reduced diameter along the debarked log, which influences log classification and optimization by reducing available wood for lumber production. As to pressure radially applied to cutting tools, values for that parameter may be assigned according to log physical characteristics as well as environmental and storage conditions. At sawmill, pressure values are typically determined according to wood species, average log diameter and log surface log temperature state (frozen or non-frozen), and the radial pressure may be adjusted during debarking as the debarking log diameter is changed. When the radial pressure is set at low value to prevent fiber loss, more residual bark is thus observed on the debarked log surface. Log feed speed is considered as an important factor of debarking yield, and that parameter is usually kept at a high value at sawmill. As to ring rotational speed, a high value assigned to that parameter increases tool arms centrifugal forces and decreases tool reaction time, which factors are beneficial to debarking yield increases as reported by Laganiere, B. et al. in "Effects of radial force and tip path overlap on the ring debarking efficiency of frozen balsam fir logs", Forest Products Journal, vol. 55, No. 3. 2005. As a result of combined effects of log feed and ring rotation, consecutive debarking tool tip path overlap occurs during debarking, and to ensure complete bark coverage by the tips, an overlap factor over 10% has been suggested by Lapointe, J. A. in "Optimizing the operation of ring debarkers. Research Memorandum", Project No. 76-0207-01. Domtar Research Center, Senneville, Qc, Canada. 1976, pp. 45. For a given value of log feed or ring rotational speed, the tool tip path overlap can be increased by decreasing the ring rotational or feed speed, respectively.

Generally, operation of the rotary ring debarker is based on experience of sawmill operators, the operation parameters such as pressure applied to the cutting tools, log feed speed and ring rotational speed being set up for different wood species and log temperature states (frozen or non-frozen). For years, the quality control at the output end of known debarking equipment has been generally limited to visual control and classification by an operator, which is not precise and results in a relatively high classification error rate. In some lumber mills, samples are periodically selected in order to determine the amount of bark into wood chips or the amount of fiber present into bark. These procedures give merely rough indications of debarker performance that merely allow trend monitoring, without providing accurate quality control. For years, many automated system have been proposed to automate debarking quality detection generally based on sensors measuring surface reflectivity of the debarked logs or samples thereof, such as disclosed in the following patent publications: U.S. Pat. Nos. 2,769,468; 5,247,978; 5,274,244; 5,335,790; 6,137,894; 6,166,393; 6,493,076; 6,526,154; 6,614,041; 6,539,993; and US 2010/236664. However, surface reflectivity alone cannot discriminate all of the various characteristics associated with debarked surface quality to allow an accurate control thereof. More recently, the use of three-dimensional profile data for detecting surface defects on debarked logs has been proposed by L. Thomas in "Automated detection of surface defects on barked hardwood logs and stems using 3-D laser scanned data" Virginia Polytechnic Institute and State University, Virginia, U.S.A., September 2006. However, the contour-based detection approach as taught by Thomas is limited to the identification of defects characterized by significant height changes, such as defective knobs and depressions, the detection of which defects cannot allow an accurate control over the quality of debarking.

SUMMARY OF THE INVENTION

The following presents a simplified summary in order to provide a basic understanding of one or more aspects of the invention. This summary is not an extensive overview of the invention, and is neither intended to identify key or critical elements of the invention, nor to delineate the scope thereof. Rather, the primary purpose of the summary is to present some concepts of the invention in a simplified form as a prelude to the more detailed description that is presented later.

The object of the proposed invention is to obtain for each wooden log under or after debarking operation, information on main parameters related to the debarking quality of the log surface, including fiber loss and residual bark. That quality indicative information can be generated on a continuous basis at the output end of the debarker, providing an objective assessment of the quality performance in real-time in view of target productivity, and may then be used by the operator to perform optimal adjustments of the debarker operating parameters when necessary. Furthermore, knowing or measuring upstream the intrinsic characteristics of the each log entering the debarker such as diameter and wood species, its environmentally influenced characteristics such as temperature and moisture content, as well as debarker tool data such as angular position of cutting tools and wear level of tools, information on fiber loss and residual bark obtained while debarking or at the output of debarker may be used to automatically perform in feedback the required debarker adjustments, such as magnitude of controlled pressure applied to cutting tools, ring rotational speed and log feed speed, to provide optimal performance in real time.

According to the above object, from a broad aspect of the invention, there is provided a method for detecting the quality of debarking at the surface of a wooden log, comprising the steps of: i) measuring a three-dimensional profile of at least a portion of the log surface to generate corresponding profile image data; ii) processing the profile image data to generate data indicative of the texture of the log surface; and iii) analyzing the texture data to generate resulting data on parameters related to the debarking quality of the log surface, said parameters including fiber loss and residual bark.

According to the above object, from another broad aspect of the invention, there is provided a system for detecting the quality of debarking at the surface of a wooden log. The debarking quality detecting system comprises a three-dimensional profile measuring unit for scanning at least a portion of the log surface to generate corresponding profile image data; data processing means receiving the profile image data to generate data indicative of the texture of the log surface; and data analyzing means receiving the texture data to generate resulting data on parameters related to the debarking quality of the log surface, said parameters including fiber loss and residual bark.

According to the above object, from a further broad aspect of the invention, there is provided a software product data recording media in which program code is stored, the program code will cause a computer to perform a method for detecting the quality of debarking at the surface of a wooden log, from three-dimensional profile data of at least of portion of a surface of the log, which method comprising the steps of: processing the profile image data to generate data indicative of the texture of the log surface; and analyzing the texture data to generate resulting data on parameters related to the debarking quality of the log surface, said parameters including fiber loss and residual bark.

According to the above object, from another broad aspect of the invention, there is provided a method for detecting the quality of debarking at the surface of wooden logs and for controlling a debarking process applied to the wooden logs on the basis of said debarking quality, comprising the steps of: i) measuring a three-dimensional profile of at least a portion of the surface of one of the logs to generate corresponding profile image data; ii) processing the profile image data to generate data indicative of the texture of the log surface; iii) analyzing the texture data to generate resulting data on parameters related to the debarking quality of the log surface, said parameters including fiber loss and residual bark; and iv) controlling the debarking process applied to a next one of the logs using the resulting data.

According to the above object, from a still further broad aspect of the invention, there is provided a system for detecting the quality of debarking at the surface of wooden logs and for controlling a debarking process applied to the wooden logs on the basis of said debarking quality, comprising a three-dimensional profile measuring unit for scanning at least a portion of the log surface to generate corresponding profile image data, data processing means receiving the profile image data to generate data indicative of the texture of the log surface, data analyzing means receiving the texture data to generate resulting data on parameters related to the debarking quality of the log surface, said parameters including fiber loss and residual bark, and means for controlling the debarking process applied to a next one of said logs using said resulting data.

According to the above object, from still another broad aspect of the invention, there is provided a software product data recording media in which program code is stored, said program code will cause a computer to perform a method for detecting the quality of debarking at the surface of wooden logs and for controlling a debarking process applied to the wooden logs on the basis of said debarking quality, comprising the steps of: i) measuring a three-dimensional profile of at least a portion of the surface of one of the logs to generate corresponding profile image data; ii) processing the profile image data to generate data indicative of the texture of said log surface; iii) analyzing the texture data to generate resulting data on parameters related to the debarking quality of the log surface, said parameters including fiber loss and residual bark; and iv) controlling the debarking process applied to a next one of the logs using the resulting data.

BRIEF DESCRIPTION OF THE DRAWINGS

Some illustrative embodiments of the debarking quality detection and control method and system will now be described in view of the accompanying drawings in which:

FIG. 3 is an isometric view of a debarking line provided with a debarking quality detection and control system according to one embodiment as described in detail below;

FIG. 3A is a partial isometric view of the debarking quality detection and control system of FIG. 3, showing details of the profile measurement unit;

FIG. 4 is a top view of the debarking line and debarking quality detection and control system of FIG. 3;

FIG. 4A represent a log feeding unit disposed upstream the debarker of FIG. 4;

FIG. 5 is a side view of the debarking line and debarking quality detection and control system of FIG. 3;

FIG. 7 is a schematic block diagram of the debarking quality detection and control system of FIG. 3, representing its computer-based hardware and software components;

FIGS. 11A to 11C are scaled images respectively derived from previously cleaned intensity, width and profile images of FIGS. 8A to 8C;

FIG. 12 is an image resulting of a flattening task as performed on the scaled profile image of FIG. 11C;

FIGS. 13A and 13B are respectively horizontal and vertical edge detected images as obtained from the flattened profile image of FIG. 12;

FIG. 21A and FIG. 21B are images respectively representing the scaled intensity image (FIG. 11A) and the corrected intensity image obtained by applying a ramp function;

FIG. 22 is a filtered image obtained by thresholding the corrected intensity image of FIG. 19B;

FIGS. 23A to 23C are images respectively representing the mask indicating fiber tear areas on the log, the mask indicating enlarged bark areas on the log, and the resulting correction of the fiber tear indicating mask after removal of enlarged bark areas;

DETAILED DESCRIPTION OF THE ILLUSTRATIVE EMBODIMENTS

Figure 1:
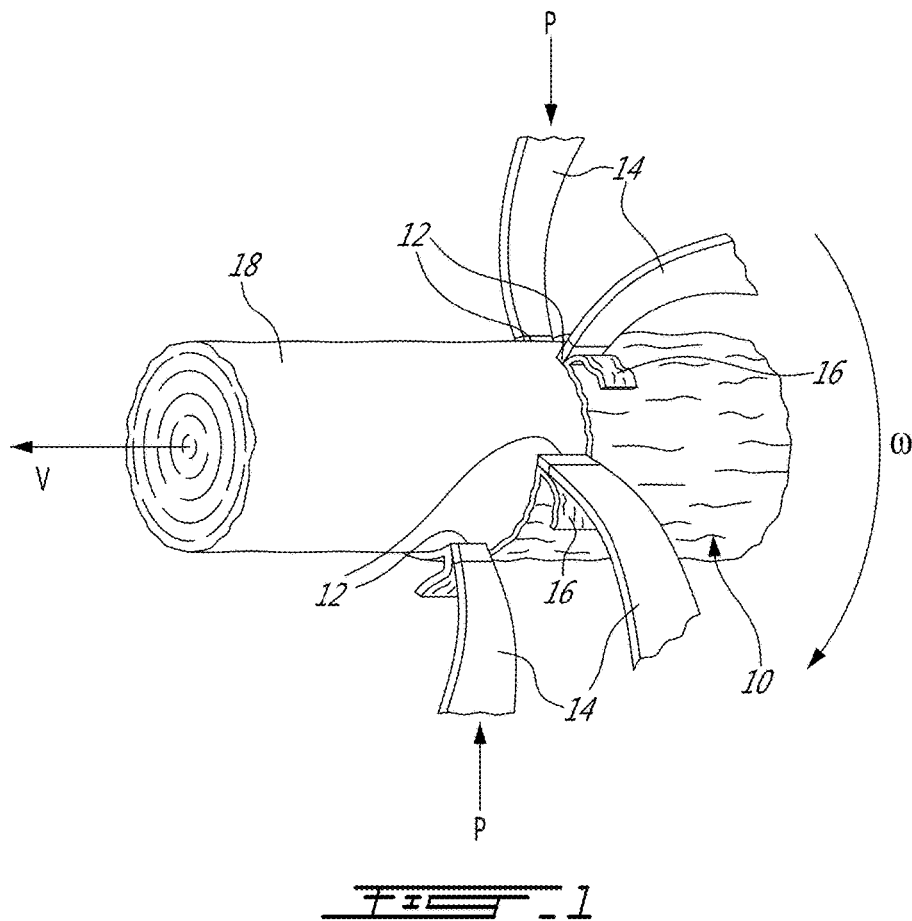
FIG. 1 represents a log being subjected to debarking through the action of cutting tools provided on a typical rotary ring debarker.
Figure 2:
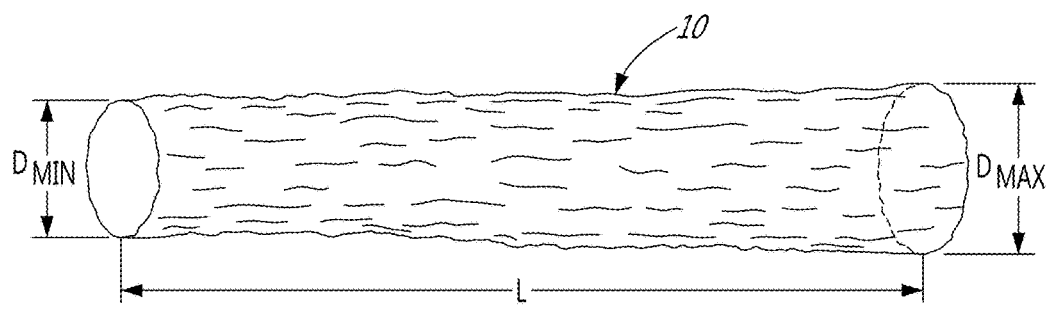
FIG. 2 represents a log to be debarked, showing its dimensional parameters.

Referring to FIG. 1, there is schematically represented a log 10 being subjected to debarking through the action of cutting tools 12 such as knifes mounted at working ends of arms 14 provided on a typical rotary ring debarker, and disposed in a circular arrangement defined by the ring. The log 10 is fed into the rotary ring debarker in a continuous mode of operation at a feed speed V and as its ring rotates at a rotational ring speed ω, the bark 16 of the log gets peeled down to the cambium layer, herein designated as the debarked surface 18, through the action pressure P radially applied to tools 12. It can be seen that the log 10 is typically characterized by a length L, a minimum log diameter $D_{MIN}$ and a maximum log diameter $D_{MAX}$ as shown in FIG. 2, which parameters influence log taper shape, and may be considered by the predictive model of debarking process as will be explained below in detail.

Figure 6:
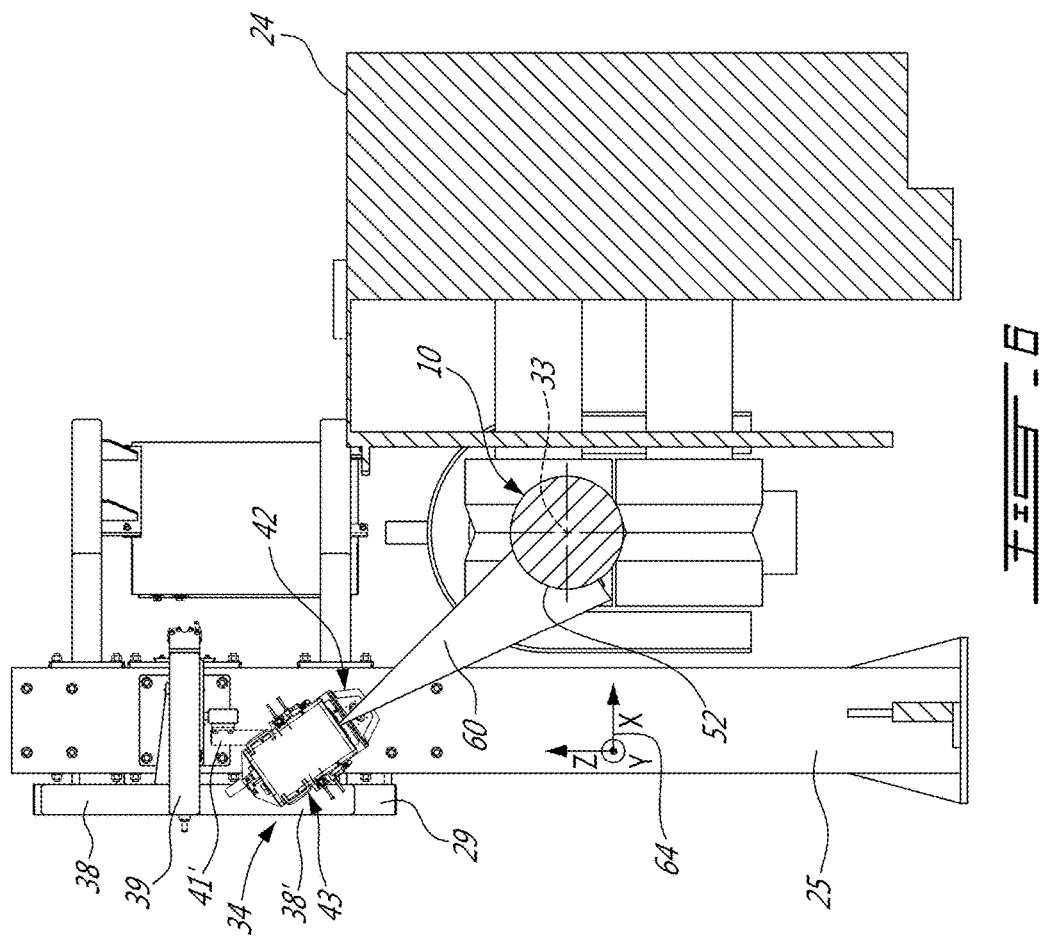
FIG. 6 is a cross-sectional end view of the debarking line and debarking quality detection and control system of FIG. 3 according to section lines 6-6 shown in FIG. 5.

Referring now to FIG. 3, a typical debarking line generally designated at 20 is provided with a debarking quality detection and control system 22 aligned with the output end of a debarker 24 provided with a conveying system including infeed and outfeed devices 21 and 21' each using front and rear pairs of vertically aligned V-shaped press rolls 23, 23' and 26, 26' for transporting a log 10 along a travel path axis 33 while being processed by debarker 24, the debarked log being received on an exit conveyer 11 within a shielding tunnel 15. The debarker 24 may be a rotary ring debarker such as model A5 supplied by Nicholson Manufacturing Ltd (Sidney, BC, Canada), or any other appropriate debarker available in the marketplace. The detection system 22 includes a profile measuring unit 34 held above the travel path axis by a pivoting frame 28 mounted to a vertical stationary column 25 standing from the plant floor and rigidly secured therereto, and using a hinge assembly 27, enabling an operator to move the profile measuring unit between a working position as shown in FIG. 3 and a withdrawal position allowing the operator an access to the outfeed device 21'. The pivoting frame 28 includes a post 29 to which are laterally secured upper and lower pairs of lugs 32, 32' provided with aligned bores adapted to receive upper and lower hinge-pins 35, 35', a respective end of which in turn engaging with lower and upper hub bracket 36, 36' secured to the column 25. The pivoting frame 28 further includes a boom 37 rigidly secured at a base end thereof to the post 29 with reinforcing members 38, 38', and having a free end to which is attached a subframe 39 having a bottom portion forming an adjustable support 40. The boom 37 can be firmly held to the working position using a locking device 54 secured to the column 25 as shown in FIG. 4. The support 40 is provided with a plurality of parallel elongated openings for adjustably receive and secure first and second holders 41, 41' to which are respectively attached a camera assembly 42 and a laser source assembly 43 as part of the profile measuring unit 34, as better shown in FIG. 3A. The three-dimensional profile measuring unit 34 is used for scanning at least a portion of the log surface to generate corresponding profile image data, to be analyzed in order to detect debarking quality of the log surface in terms of quality parameters including fiber loss and residual bark, as will be described later in more detail. The camera assembly 42 includes an enclosure 44, which is respectively shown in FIGS. 5 and 3A with and without its cover 45, for containing and protecting from the log processing environment a digital 3D camera 62, which enclosure 44 is adapted to be secured to holder 41 through a mounting arrangement 46 allowing positional and angular adjustment of the optical sensing field 56 with respect to a scanning plane transverse (i.e. parallel to plane X-Z in reference system 64) to the travel path axis 33 as shown in FIG. 6. The camera enclosure 44 has a base wall 47, as well as a front and rear wall 48, 48' defining a peripheral edge, the front wall 48' having an opening 49 protected by an optical element made of light transparent material such as glass or plastic. The enclosure 44 further has a device 50 for mounting the camera 62 within the enclosure such that it has its optical sensing field 56 directed toward opening 49 for passing therethrough. Power supply line, control and scanning output data lines as well as a vortex tube for cooling (not shown), can be introduced within enclosure 44 through appropriate apertures provided on rear end wall 48. Turning to FIG. 5, the enclosure 44 further includes an enclosure cover 45 having a closing edge adapted to mate with the peripheral edge defined by the enclosure walls to provide full closing of the camera mounting space, while allowing full access to this space when the cover 45 is brought to an open position after release of a clamp 51 provided on the enclosure 44. Conveniently, the laser source assembly 43 includes an enclosure 44' of a design similar to the camera enclosure 44 as described above, which enclosure 43 is respectively shown in FIGS. 5 and 3A with and without its cover 45', for containing and protecting from the log processing environment a laser source 58. The enclosure 43 is adapted to be secured to holder 41' through a mounting arrangement 46' allowing positional and angular adjustment of the fan-shaped laser beam 60 defining the scanning plane, as better shown in FIG. 6.

As better shown in FIG. 3A, the profile measuring unit 34 has its sensing field 56 transversely directed toward travel path axis 33 and defining a profile scanning zone 55 associated with the log surface as intersected by the optical sensing field 56, to generate profile image data related to the scanned log surface, in a direction along axis Z according to reference system 64, which direction Z being orthogonal to a reference plane X-Y parallel to the travel path axis. The profile sensor unit may conveniently use a same laser triangulation ranging approach as disclosed in U.S. Pat. No. 7,429,999 issued to same assignee as of the present invention. In the presently described embodiment, the longitudinal axis generally defined by the log 10 is maintained substantially aligned or parallel to the travel path axis 33, which is collinear or at least parallel to Y axis of the reference system 64. In the present embodiment, while scanning along the log longitudinal axis is conveniently obtained as a result of a relative movement between the conveyed log and the stationary profile measuring unit 34, it is to be understood that longitudinal scanning could also be obtained by using a profile measuring unit capable of moving lengthwise with respect to a stationary log, for example in a case where a drum debarker is used for debarking logs in batches. The laser source 58 included in the profile measuring unit 34 is used to direct, at angle with the optical sensing field 56, the fan-shaped laser beam 60 toward profile scanning zone 55 to form a reflected laser line onto the log surface, corresponding to a scanned zone 52. The 3D camera 62 is used to capture an image of the reflected laser line or scanned zone 52, the output of which camera 62 being fed through its processing unit and output line through link 57 as shown in FIG. 3, to an image acquisition unit as part of computer 66 which generates profile image data in a manner that will be described in detail below in view of FIG. 7. A digital 3D camera such as model C3-2350 from Automation Technology GmbH (Bad Oldesloe, Germany) integrating a processing module for profile-related output generation, may be used. A laser such as model ILS-670-500-A-20°, 500 mW-670 nm, from Osela Inc. (Pointe-Claire, Quebec, Canada) may be used, with a transverse fan angle of about 30°. It is to be understood that any other appropriate camera of laser available in the marketplace can be used. The image acquisition unit may be based on hardware available on the marketplace, such as model Odyssey PCI e-x4ecl data acquisition boards from Matrox (Dorval, Quebec, Canada). An electrical supply unit for the profile measuring unit 34 can be contained in a cabinet 68 secured to the column 25 by frame member 53.

Although the scanning plane is defined by the fan-shaped laser beam 60 in the embodiment shown in FIG. 3, it is to be understood that in another embodiment, the scanning plane could be defined by the optical sensing field of the camera, provided the fan-shaped laser beam is still directed at angle with the optical sensing field to allow triangulation. Moreover, while a fan-shaped laser beam is conveniently used in the shown embodiment to form a reflected laser line, a plurality punctual laser beams directed to corresponding points of the log surface may also be used to generate profile image data.

It can be appreciated from FIG. 3A that log 10 moving along the travel path axis 33 in a direction indicated by arrow 41 parallel to axis Y of reference system 64, has its surface intersecting the sensing field 56 at a surface zone onto which laser beam 60 reflects light toward camera 62. The portion of the scanned surface for which three-dimensional profile is measured can be comprised of several scanned zones 52 transversely extending along the circumference the log, at several corresponding locations along the travel path axis 33. Experiences have shown that reliable measurements can be obtained with a scan zone representing about 15% of the log circumference, applied at least every 2.5 mm along the travel path axis 33. This result is based on the fact that for logs processed with a typical rotary ring debarker, debarking quality characteristics are substantially uniform along the log circumference at any given scanning position, so that the detection obtained with a limited scan zone is substantially representative of the entire log circumference. It is to be understood that a higher scan zone ratio could be used for debarked logs showing significant variations of debarking quality characteristics along their circumference. While only a portion of the log surface is conveniently scanned in order to optimize processing and analyzing time, full surface (full circumference) of a log could also be scanned if necessary. It is also to be understood that even a single three-dimensional profile measuring unit 34 is involved in the embodiment shown in FIG. 3, a plurality of such units may be integrated to simultaneously scan several sets of zones of the log surface distributed along the circumference the log, by adapting the pivoting frame accordingly, or by providing a separate supporting structure. Furthermore, while the conveying stability of each log is usually maintained by the feeding device 21 provided on the debarker 24 to prevent vibration causing log translation and rotation under the impact of the rotary cutting tools, a small residual translation or rotation of the log along or about its longitudinal axis would not adversely affect the three-dimensional profile measurement of the scanned surface portion. The function of the processing unit integrated in the camera 62 consists of deriving the profile-related output data from two-dimensional images captured by the camera, involving calculation of the centers of gravity (centroids) of the laser beam image, or any other appropriate algorithm. The processing module can be wholly or partially integrated into the camera 62, or be part of a separate data processing unit interfaced with the camera to receive and process two-dimensional image data therefrom.

As will be explained below, to provide a further indication of the residual bark, the debarking quality detection and control system 22 may include means for measuring light reflection from the inspected log surface portion to generate corresponding reflected light intensity image data. Conveniently, the same camera 62 may be used to obtain such intensity image data, wherein each pixel value represents the intensity value measured at a given position along the laser line, which intensity value is obtained through integration in the direction transverse to the laser line, i.e. along its width extending parallel to the direction of axis X in the reference system 64. Optionally, the same camera 62 may be used to obtain further image data wherein each pixel value represent the width of the laser line at the given position, on the basis of which further image analysis may be performed to detect debarking quality. As an alternative, a separate image sensor unit (not shown) could be provided for measuring light reflection from the inspected log surface portion, which separate unit would include a 2D digital camera having its output being fed to the image acquisition unit, generating a two-dimensional intensity image of the laser line, or having its own illumination source such as set of fluorescent tubes. Although a monochrome camera could be used to obtain the required intensity image data, an equivalent intensity image signal such as luminance could also be obtained from a color camera, and the color signal components may provide additional information about other characteristics of the log surface. The debarking quality detection and control system 22 also includes profile image data processing and analyzing means in the form of a programmed computer 66, which may be installed in a control room remote from the debarking line, by using an appropriate link between the output of camera 62 and the input of computer 66. From the profile image data, the data processing means generates data indicative of the texture of the log surface, which data is then sent to the data analyzing means which generates resulting data on main parameters related to the debarking quality of the log surface, in terms of detected fiber tear and residual bark, which data can be displayed to the operator.

As will be explained later in more detail, the computer 66 can be connected to the controller (PLC) 67 of the debarker 24 using link 70 to receive information on debarker operating parameters that could be used by the programmed computer 66 or displayed to the operator. It has been observed that for a same wood species and when debarking operation parameters are kept constant, some physical characteristics such as log diameter, taper shape and environmental conditions such as log temperature state (frozen or non-frozen) have significant influence over debarking quality. Optionally, and as will be explained below in more detail in view of FIGS. 25 to 27, the computer software may include a control module using information on fiber loss and residual bark as measured, to provide commands enabling the controller 67 to send through link 72 feedback control signals for the required debarker adjustments providing optimal performance in real time, on the basis of input data related to intrinsic characteristics of each log entering the debarker such as wood species information, mean log diameter, taper shape indicator, and environmentally influenced characteristics such as log surface temperature and moisture content, coming from other sensors or data entry means through link 83. For that purposes, as shown in FIG. 4A in view of FIG. 4, the debarking line 20 may be provided with a log conveyer 13 located upstream the debarker 24, and having an outfeed end 106 aligned with the travel path axis 33, so that a next log 10' to be debarked is transported toward the front V-shaped press rolls 23, 23' at the infeed end of the debarker 24. Located adjacent the conveyer 13 is a log diameter and length measurement device 17 having its output operatively connected to the controller 67 shown in FIG. 3 for sending thereto signals indicative of the diameter and length of the log 10' as it is moved past the measuring device 17. Any appropriate non-contact sensor may be used as diameter and log length measurement device 17, such as laser light curtain sensor of type P, 600 mm, supplied from ScanMeg Inc. (Boisbriand, Quebec, Canada), which includes a laser emitter module 19 facing a first side of conveyer 13 so as to direct laser beams toward the travel path axis as intersected by log 10', and a laser detecting module 19' facing the other side of conveyer 13 so as to capture laser light unobstructed by log 10' along its radial dimension. Conveniently, a mean diameter can be derived from measurements of minimum log diameter $D_{MIN}$ and a maximum log diameter $D_{MAX}$ as shown in FIG. 2, or can be derived from a plurality of measured diameter values obtained along the log 10' from its leading end to its trailing end. Knowing the preset feed speed of conveyer 13, the log length L may be easily derived from the output signals of detecting module 19', based on detection of the abrupt signal intensity decrease associated with entry of the log leading end through the sensing field of the device 17, and the abrupt signal intensity increase associated with exit of log trailing end out of the device sensing field. Moreover, the spacing between consecutive logs can be measured in a similar way, which spacing measurement may be used by the computer for synchronization purposes. Conveniently, log taper shape indicator may be derived as follows:

$$T = \frac{(D_{MAX} - D_{MIN})}{L} \quad (1)$$

It should be understood that the log taper shape indicator may also be derived from a plurality of measured diameter values obtained along the log from its leading end to its trailing end. Furthermore, for improving the debarking control as will be explained below in detail, there may be provided a non-contact temperature sensor 63 conveniently located adjacent the conveyer 13 for measuring the temperature at the surface of the next log 10' to be debarked, to send a temperature indicative signal to the controller 67 shown in FIG. 3. Any appropriate non-contact temperature sensor such as model MI-D-10-LT-CB3 supplied from Raytek Corp. (Santa Cruz, Calif., USA) may be used. The location of conveyer 13 with log diameter and length measuring device 17 and temperature sensor 63 is determined so as to allow sufficient processing time to the computer 66 to perform signal processing and analyzing tasks of a currently debarked log 10, as well as to allow some computation for debarking control purposes as will be explained later in detail. Fiber loss and residual bark levels can be estimated by comparing log surface areas respectively characterized by fiber loss and residual bark with the log surface considered, by calculating a ratio (or percentage) of the log surface where each of these characteristics has been detected, to the corresponding surface of the log or log section considered. Debarking quality is differently affected at leading and trailing ends of a log as compared with its middle, body section, due to the cutting tool attack under pressure that occurs against the log leading end, and the cutting tool retracting that occurs at the log trailing end. Therefore, according to preset limits defining leading end, trailing end and body sections of the log, a representative portion of the log surface for each of these three log sections can be scanned, to provide corresponding three sets of quality parameter data, from which fiber loss level and residual bark level are estimated for one or more of said sections, or for the whole log surface. For example, for a 4.88 m (16 ft) log, both the leading end and trailing end limits can typically be of 0.6 m (2 ft), leaving 3.66 m (12 ft) for the log body section. Furthermore, a ratio of the optimally debarked surface, i.e unaffected by fiber loss or residual bark, to the log surface considered can be easily calculated (optimal debarked surface level in %). Optionally, predetermined weighting factors can be assigned to the sections on the basis of their relative importance in debarking quality detection, which factors are applied to estimate fiber loss level and residual bark level data.

Furthermore, fiber tear and residual bark can be visually represented in the form of an image generated from the resulting data, which represents areas of the log or log section surface considered, where fiber loss and residual bark have been respectively detected, as will be explained below in more detail in view of examples.

As another alternative, a knowledge-based system such as an expert system fed by detected quality data may be provided in the computer software to assist the operator to make decisions so as to perform a more efficient control of the debarking process.

Referring now to FIG. 7, the debarking quality detection system 22 is schematically represented with its computer-based hardware and software components. The image acquisition unit is connected to the camera processing unit 59 to receive 3D information and to generate corresponding profile image data, in correspondence with physical sensed location on the inspected log surface. For so doing, the image acquisition unit 65 includes a frame grabber 74 programmed to integrate all necessary functions to associate 3D information with sensed location data for each scanned surface portion as well as all processing functions aiming at standardization of image specifications. As to the sensed location along Y axis on the inspected log surface, although the operation of debarking line 20 is less complex when each log is fed by conveyer 26 to the system 22 at a predetermined, substantially uniform speed along travel path axis 33 which may typically reach 140 linear m/min, a varying speed or position/time profile could also be used. The speed or position/time profile operation of the system according to actual speed conditions can be performed by providing means for measuring the actual speed or position/time profile of the moving log, such as a rotary encoder (not shown), or any appropriate non-contact detector (photocell array, laser velocimeter) disposed at a proper location along the travel path axis 33, coupled to conveyer 26 and sending its output through link 69 to the data acquisition unit 65. Alternatively, the data acquisition unit may use the time synchronization approach, as disclosed in co-pending U.S. patent application Ser. No. 12/693,693 as published under no. US 2010/0188500A1, wherein updating time data is used to perform sensor output data assembling with corresponding sensed location data related to log surface. The image resolution along X axis is intrinsic to pixel density of the CCD array provided on the digital camera 62 and to any sub-pixelation algorithm used by the processing unit 59, which resolution along X is typically of 0.33 mm/pixel with j=1280 pixels for a C3-2350 camera according to the settings used. The scanned log being displaced perpendicularly with respect to the CCD array of camera 62 to form a two-dimensional image, the resolution along Y axis is determined by the relative distance traversed by the log between two successive image acquisition steps, which resolution along Y is typically from about 2 to 2.5 mm/pixel. Hence, image resolution along X axis can be typically up to six times resolution along Y axis, with a number of lines i depending on the actual length of the scanned log as well camera settings used. For example, i≈1400 for a log length of about 2.44 m. For image displaying and interpretation purposes, such resolution difference may be compensated by scaling, as will be explained later in view of an example.

Prior to its operation, the camera 62 must be optically calibrated according to the supplier specifications to ensure image sensing accuracy, using any appropriate procedure involving reference charts of predetermined image intensity levels, such as a black-white-grey chart. Furthermore, the frame grabber is programmed to apply spatial calibration of the measured 3D information in order to make accurate correspondence between the measured coordinates with respect to the camera reference system (i.e. in pixels), and the "world" coordinates (e.g. in mm) with respect to the physical reference system 64. For so doing, a calibration approach such as disclosed in U.S. Pat. No. 7,429,999 issued to same assignee as of the present invention, or any other appropriate calibration technique, may be programmed in the frame grabber including a proper interface for the operator to carry out calibration tasks. As a convention, a point (i, j) in a profile image is associated with a corresponding z profile coordinate along Z axis, wherein each line i of the image represents a y coordinate along Y axis which is parallel to travel path axis 33, and wherein each column j of that same image is associated with a CCD array column at a x coordinate along X axis.

As a result of applying spatial calibration, the measured centroid position coordinates (in pixel) for each column j of the camera CCD array is converted into "world" reference coordinates. Conveniently, the z coordinates are defined with respect to the central point of the calibration target that has been used in the calibration procedure that preceded operation of the system. Since initially, each coordinate j does not correspond to a constant, actual distance on the log surface with respect to x axis, image data as expressed with respect to the camera reference system are corrected by converting each j coordinate with respect to a physical reference, and each i within the same image data is associated to a constant physical distance in transverse direction along x axis. Conveniently, the results of spatial calibration may be generated in the form of image data complementary to profile image data and light intensity image data, so that three images associated with the scanned surface are basically created, the first representing z coordinate (profile) values of the detected centroids along Z axis, the second representing reflected light intensity values corresponding to the centroids, and the third representing x transverse coordinate values of the centroids along X axis. As mentioned above, a fourth image may be optionally created, representing laser line width at corresponding centroids. The frame grabber is programmed to apply predetermined thresholds for assigning a preset value to pixels generated by the CCD array, which physically cannot correspond to a point of log surface, such as points associated with conveyer parts, and thrown or hanging bark fragments. The preset value, such as 0 or 9999, is chosen to be far from the valid pixel range, extending typically from a positive minimum value to a value between 100 and 1500 for example, to clearly discriminate valid pixels from invalid pixels. It is to be understood that the valid pixel range is influenced by many factors depending from the camera settings and calibration, as well as from the characteristics of the logs under inspection, such as wood species, diameters and lengths.

Figure 8A:
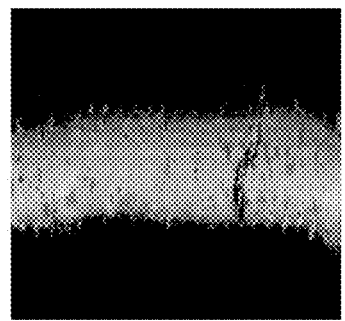
FIGS. 8A to 8D are exemplary images respectively representing light intensity, laser line width, profile and transverse coordinate data associated with a scanned log.
Figure 8B:
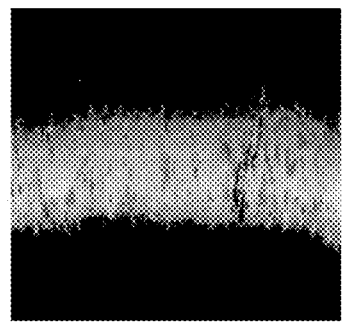
Figure 8C:
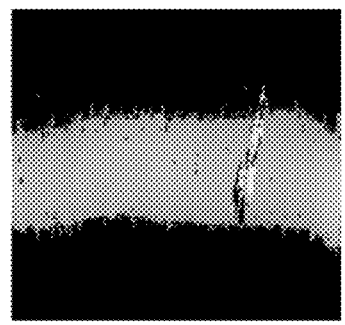
Figure 8D:
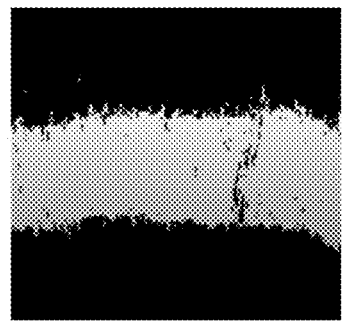

Exemplary resulting images as generated by the frame grabber 74 after scanning of a log are shown in FIGS. 8A to 8D with respect to X and Y axis of the chosen reference system, respectively representing distance unit (e.g. mm) and pixel unit, each image containing typically $179.2 \times 10^3$ pixels (1280×1400). In FIG. 8A, light intensity image data are represented, wherein the values of intensity are conveniently indicated through various grey levels extending within the range of measured values. In FIGS. 8B, 8C and 8D respectively, laser line width, profile image and transverse coordinate data are represented according to a same grey level-based format.

All said image data as generated by frame grabber 74 are available at an output of the image acquisition unit 65 to be communicated through link 71 to the input of a detection module 76, whose ultimate function consists of generating specific information related to the debarking quality of the surface of the inspected log, namely fiber loss and residual bark, to generate corresponding output data through link 73 to a database 78. First, the profile image data is processed to generate data indicative of the texture of the log surface, and then, the texture data is analyzed to generate the resulting debarking quality data. For so doing, the detection may call for appropriate processing and analyzing subroutines respectively identified at 84 and 86 in FIG. 7, which subroutines may be in the form of DLL files containing appropriate code for performing the desired functions, which will be described below in detail in view of an example. Although a DLL architecture may be conveniently used as a basis for modules and other components of the computer program, any other architecture such as COM architecture may also be used for a same purpose. All data communication links described above may be implemented into a data communication network to provide data exchange between the database 78, the various modules and components of the detection system 22, as well as the debarker and other sensors/data entry means through controller 67. Such a communication network can further be connected to a plant control computer linked to the controller 67 and allowing an operator to make input parameter settings for the detection module 76.

An exemplary implementation of processing and analyzing techniques capable of generating texture data will now be explained in detail. However, it is to be understood that any other appropriate processing and analyzing techniques can be used by the person skilled in the art of image data processing for the same purpose.

Figure 9:
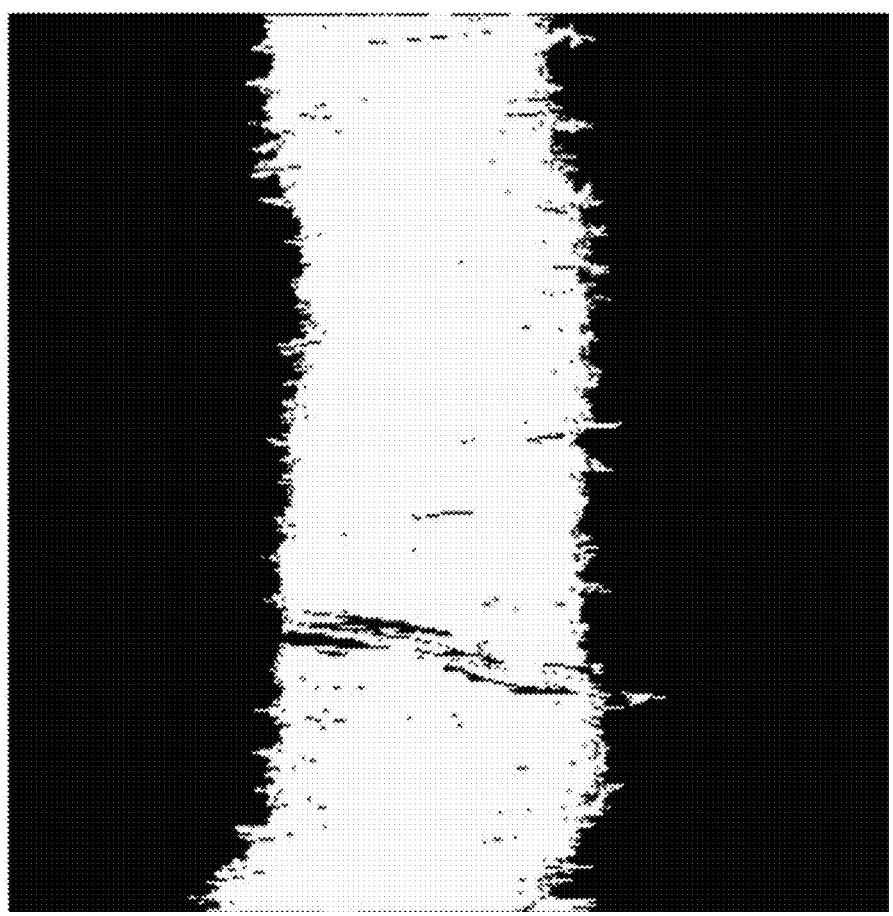
FIG. 9 is an example of binary mask image as obtained by segmentation of the image data represented in FIGS. 8A to 8D.

As a first processing task, a segmentation subroutine is called for performing morphological segmentation of the image data, in order to produce a binary mask image (referred to below as "mask_valid") wherein a valid pixel is assigned a value of "1", while any invalid pixel value is assigned a null value "0". For so doing, any of the intensity, laser line width, profile image or transverse coordinate image data can be used as starting data, since all of them have been assigned the same preset value for invalid pixels. The resulting binary image is then further processed by erosion using an appropriate structuring element of a few tens of lines by a few columns (e.g. matrix of 41×1 pixel) to move away from the edges inward, and outside pixels are cleaned to remove noise by applying an appropriate closing structural element of a few lines by a few columns (e.g. matrix of 5×5 pixel), to retain in the data only pixel values likely to be associated with a surface within the perimeter defined by the scanned log. Finally, the segmentation is completed by applying a structural element defining a threshold pixel area (e.g. 5000 pixel$^2$) to eliminate from the binary image very small blobs of pixels associated with noise, and preserve the larger blobs of valid pixels into the mask. An example of the resulting binary mask image as obtained by segmentation of the image data represented in FIGS. 8A to 8D is shown in FIG. 9, and its utility for image data analysis will be explained below in detail.

Figure 10A:
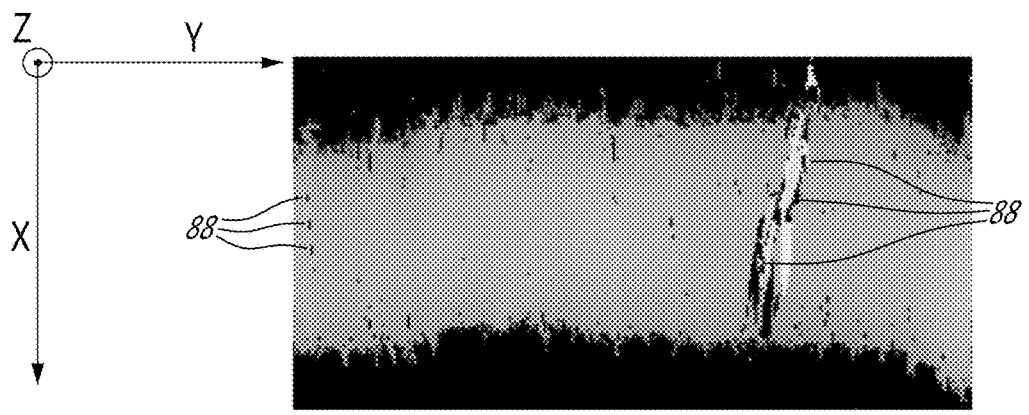
FIGS. 10A and 10B are images respectively representing the rotated profile image and a cleaned image obtained therefrom through pixel interpolation.

Referring again to the resulting image data represented in FIGS. 8A to 8D, it can be appreciated that some islands of invalid pixels appear to be surrounded by valid pixels, which islands must be also considered as noise deserving cleaning. Referring now to FIG. 10A which is a rotated and enlarged view of the profile image of FIG. 8C, some islands of invalid pixels are designated at 88, which could be wrongly detected as texture areas associated with a quality parameter such as fiber loss. Therefore, a second processing task aims at identifying the invalid pixel islands to then perform substitution by estimated valid pixel values through interpolation. For the purpose of this estimation, mean values derived from valid pixels surrounding invalid pixels of interest can be used. For so doing, an appropriate subroutine such as provided in libraries available on the marketplace such as "imfill" function of Matlab™ from Mathworks (Natick, Mass.), or "MblobReconstruct" function of MIL 9.0 from Matrox Electronics Systems (Dorval, Canada) can be used. The result of pixel interpolation task as performed on the profile image of FIG. 10A is shown in the cleaned image of FIG. 10B, wherein values of invalid pixel islands have been substituted by valid pixel values.

It can be appreciated from FIGS. 8A to 8D, 9 and 10A and 10B, that at the represented stages of processing, image data do not reflect the actual proportion of an inspected log 10 as shown in FIG. 3. As mentioned above, such image deformation is the result of higher image resolution along X axis as compared with image resolution along Y axis. From the resulting data, it is desirable to generate an image representing areas of the log surface respectively characterized by the detected fiber loss and residual bark. As mentioned above, image data measurement is performed with respect to orthogonal reference axis X and Y characterized by different resolution levels, which can be compensated by proper scaling of the resulting data, to provide a more realistic image displaying and to facilitate image interpretation by the operator. The scaling task may be performed by interpolation, whereby both scales along X and Y axis are modified according to a desired ratio, substantially without significant data alteration. For so doing, bicubic, nearest-neighbor or bilinear interpolation may be applied by calling an appropriate subroutine such as "imresize" function of Matlab™.

Figure 10B:
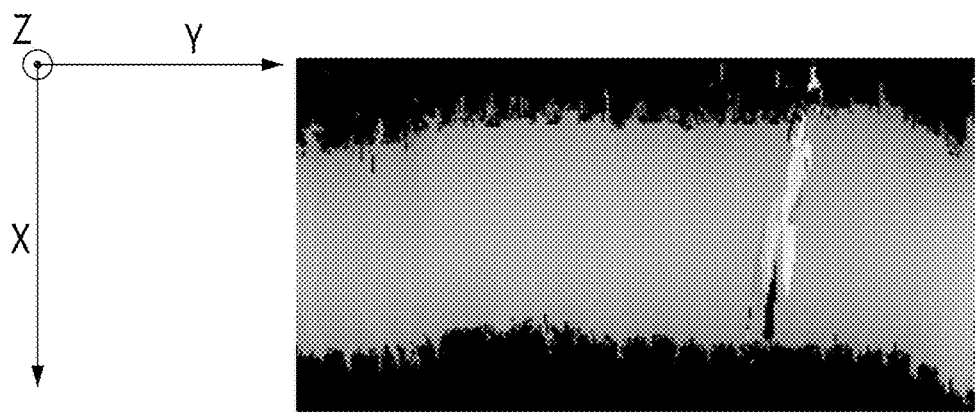

The more realistic result of scaling task as performed on the cleaned profile image of FIG. 10B using calling factors of 0.56 and 4 respectively for X axis and Y axis can be seen in the processed image of FIG. 11C. Properly scaled images derived from previously cleaned intensity and line width image data as referred to above in view of FIGS. 8A and 8B are shown in FIGS. 11A and 11B. Although image scaling is performed following the cleaning task in the present exemplary implementation, it could be performed either at an earlier or later stage of processing.

A next processing task aims at flattening the profile image data to compensate for the generally curved shape of the log surface, which could otherwise adversely affect the measurement accuracy of the quality parameters to be detected. More specifically, flattening has the effect of assigning a substantially same weight to all surface areas covered by the sensing field of the profile measurement unit, regardless of their orientation within the scanning plane. The flattened profile image data (ima_Z_f) can be performed by applying to the scaled profile image data (ima_Z) a high-pass spatial frequency filter, conveniently obtained with subtraction of low-frequency data content, by calling an appropriate subroutine such as "imfilter" function of Matlab™ making use of a Gaussian-type convoluting kernel of 32 pixel dimension with 6 as standard deviation, according to the following command:

$$\text{Ima\_Z\_f=imaZ-imfilter(ima\_Z,fspecial('gaussian',32, 6))} \quad (2)$$

The result of the flattening task as performed on the scaled profile image of FIG. 11C can be seen in the processed image of FIG. 12. It can be seen that profile data associated with the log surface as generally indicated at 90 has a collateral effect of bringing out side pixels as generally designated at 92, associated with high frequency transition out of the log perimeter. These outside pixels will be discarded for analysis purposes using the binary mask image "mask_valid" referred to above, as will be explained below in more detail. As an alternative, the profile image data flattening can be performed by applying to the scaled profile image any appropriate curve-fitting algorithm known by the person skilled in the art of image data processing.

A next processing step aims at extracting the texture characterizing the profile image data. For so doing, a technique of edge detection can been applied, which consists of detecting vertical and horizontal edges of the profile image data with respect to the substantially longitudinal axis of the log to obtain texture data. According to the convention used hereinabove using reference system 64, horizontal and vertical edges may be respectively associated with axis Y and axis X shown in FIG. 12. The detected horizontal and vertical edge are generated into the form of respective images (zhe and zve) on the basis of a Sobel convolution kernel, while reducing the dimension of the flattened image (ima_Z_f) by a predetermined factor (e.g. 0.5) to improve processing speed and reduce sensibility to noise, by calling an appropriate subroutine such as "resize" function of Matlab™ according to the following command:

$$zve = \text{resize(ima\_Z\_f; 0,5)} \otimes \begin{bmatrix} 1 & 0 & -1 \\ 2 & 0 & 0-2 \\ 1 & 0 & -1 \end{bmatrix} \quad (3)$$

$$zhe = \text{resize(ima\_Z\_f; 0,5)} \otimes \begin{bmatrix} 1 & 2 & 1 \\ 0 & 0 & 0 \\ -1 & -2 & -1 \end{bmatrix} \quad (4)$$

The result of the edge detection task as performed on the flattened profile image of FIG. 12 for horizontal and vertical directions can be seen in the edge detected images shown in FIGS. 13A and 13B.

According to a first texture analysis approach, the detected vertical and horizontal edges as part of texture data are directly compared to provide an indication of the relative ratio of fiber loss to residual bark. As a result of that direct comparative approach, a quality indicator may be obtained. For example, a useful quality indicator q can be obtained from the following image:

$$Q = \arctan\frac{zhe}{zve} \quad (5)$$

Figure 18:
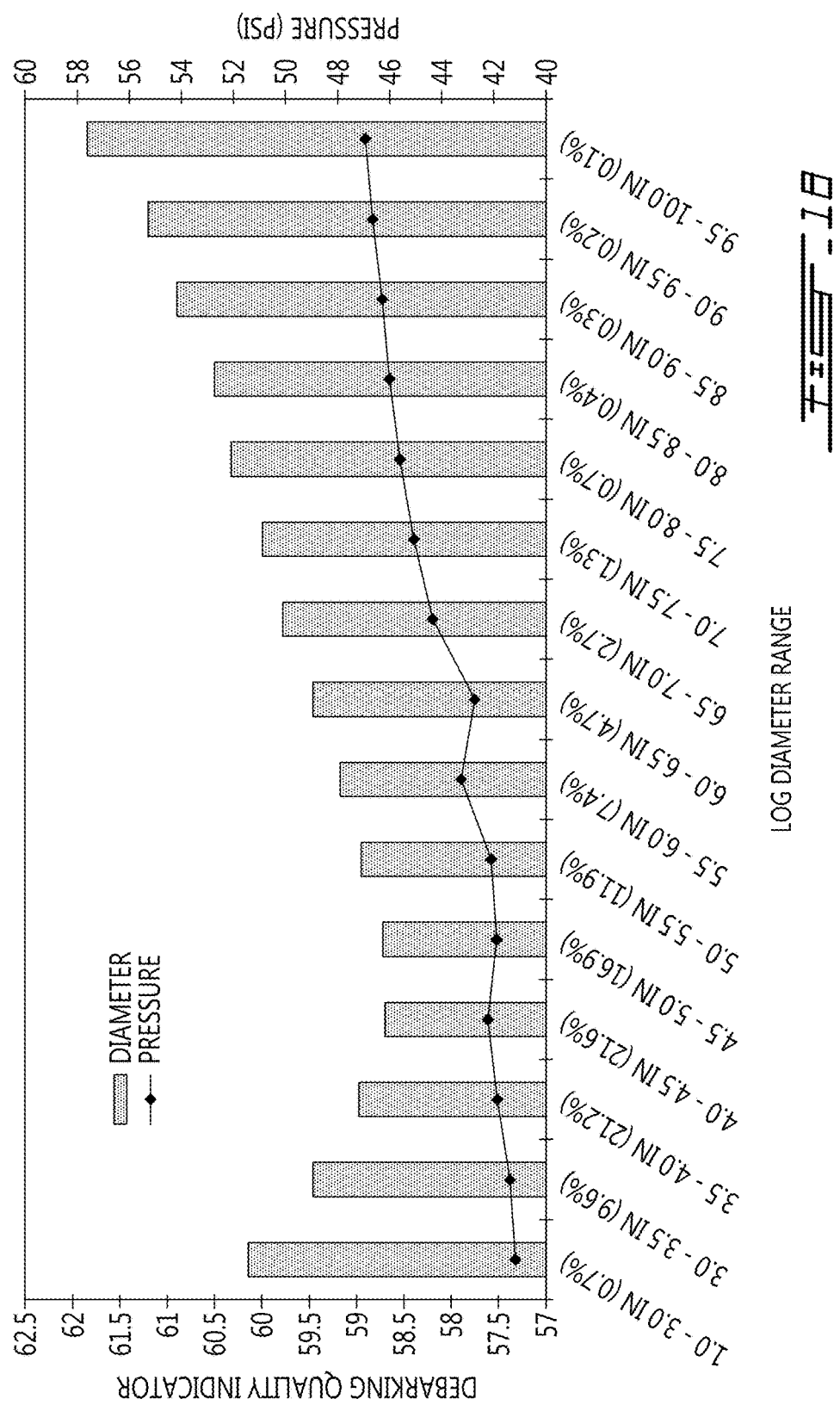
FIG. 18 is a graph presenting the values of the debarking quality indicator experimentally obtained for a number logs, and of mean pressure values applied to the debarker tools, with respect to the corresponding log diameter ranges.

For example, a mean value of image Q for the whole log surface or for a section thereof may be assigned to the debarking quality indicator q for each log scanned, to produce historical quality data, the utility of which will now be explained in the context of an example in view of FIGS. 14 and 18.

Figure 14:
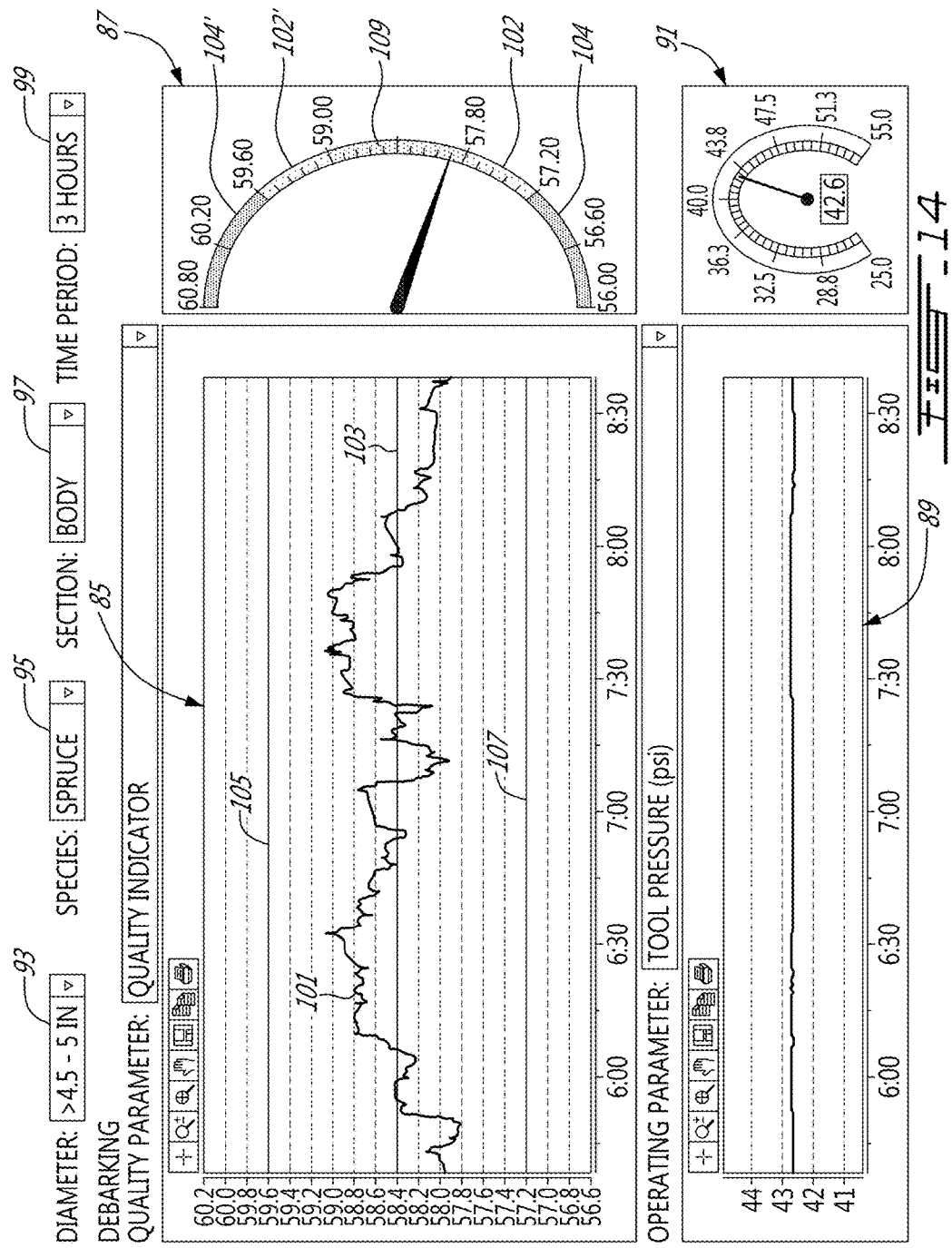
FIG. 14 is a first example of a main screen showing a quality indicator as generated by the computer program.

Referring to FIG. 14, there is shown a first example of a main screen as generated by the computer program, so that the resulting data regarding debarker performance may be directly viewed by the operator on display 80 of FIG. 7. According to this exemplary implementation, the detection results are made available to the operator through several displaying means, namely a first graph designated at 85 showing evolution of quality indicator q as the selected debarking quality parameter, with respect to the last period of production time (3 hours) as also selected by the operator, and a first analog dial 87 showing the current quality indicator value in real time. A second graph 89 is displayed for presenting evolution of a selected operating parameter, which is the mean pressure (kPa or psi) applied to the cutting tools with respect to time in the shown computer screen. A second analog dial 91 for displaying the current tool pressure value in real time is also provided, which ranges from 172 to 379 kPa (25 to 55 psi) in the example shown. Other operating parameters such as mean log surface temperature, log conveying speed, mean log diameter or log moisture content could also be displayed. Four scrolling lists at 93, 95, 97 and 99 enable the operator to select displaying criteria, namely log diameter range, species under production, log section and time period. On the first graph 85, in addition to the quality indicator curve 101, three lines are displayed designated at 103, 105 and 107. The central line 103 corresponds to the target for the desired quality parameter value as predetermined and entered by the operator, which has been set at q=58.4 in the example shown. It is desirable to assign a value to the target according to known log characteristics, and especially in consideration to the diameter range of the logs to be debarked. In practice, an optimal debarking quality implies a compromise between fiber loss and residual bark at the debarked surface of the log, and the operating conditions at which said compromise may be reached are dependent on the characteristics of the logs fed to the debarker, such as species and dryness state (moisture content). Generally, an increase of fiber loss caused by a more aggressive angle for the cutting tools may be compensated by a corresponding decrease in pressure applied to the tools. However, for a given small diameter range, e.g. <7.62 cm (3 in), logs may exhibit such a variation of dryness state so that some debarked logs present preponderant fiber loss while some others present preponderant residual bark, which result could be observed on the basis of standard deviation computing. Moreover, for a same debarking quality as qualitatively observed by the operator for two batches of logs characterized by distinct diameter ranges, the corresponding detected quality indicator values may be different, and therefore, the respective target values assigned by the operator could also be different. The lines 105 and 107 respectively correspond to predetermined upper and lower limits for the quality indicator, which may be entered by the operator in the form of a maximum deviation below and above the preset target, defining a range of acceptable debarking quality, which maximum deviation has been given a value of 1.2 in the example shown. Generally, the upper limit for the quality indicator q can be interpreted as a debarking state where an unacceptable level of residual bark onto the considered log surface is likely to be observed, while the lower limit for the quality indicator q can be interpreted as a debarking state where an unacceptable level of fiber loss onto the considered log surface is likely to be observed. Generally, the maximum deviation value is chosen by the operator on the basis of detection results corresponding to the body section of the logs, to provide a better fit with observations that can be made by the operator upon operation of the debarker. In practice, a variation in a characteristic of the logs fed to the debarking line, such as dryness state (e.g. fresh green log versus dry log) may cause a corresponding fluctuation of the quality indicator q. In cases where the current quality indicator value falls outside the preset range of acceptable debarking quality, or a trend toward such eventuality is observed, the operator may perform adjustment of a selected debarker operation parameter, such as mean pressure (kPa or psi) applied to the cutting tools, in order to have the current quality indicator value be maintained within the acceptable range as debarking is going on. Optionally, the acceptable range may be segmented in sub-ranges indicated on the scale of the first analog dial, wherein an optimal sub-range 109 extends from q=57.8 to q=59, below and above which extend lower quality (though still acceptable) sub-ranges 102 and 102' respectively from q=57.2 to 57.8 and from q=59.0 to 59.6 in example shown, and the inacceptable quality ranges beyond the sub-ranges 102 and 102' are indicated at 104 (excessive fiber loss) and 104' (excessive residual bark). Apart from the option of selecting the log section or sections to be considered for result displaying purposes, the operator may also determine the number of logs (log population, typically between 50 to 300 logs) involved in the calculation of the mean quality indicator q, conveniently based on a moving average relative to the specific time considered. A practical example making use of the debarking quality parameter monitoring will now be discussed in view of the graph shown in FIG. 18, which presents the values of debarking quality indicator experimentally obtained for 75,000 logs with respect to their corresponding log diameter ranges with percentage, as well as to mean pressure values (psi) applied to the debarker tools as set by the operator upon monitoring of debarking quality indicator values. Generally, logs of relatively small diameter may be harder to debark, as can be seen from the relatively high value of quality indicator obtained for the smallest diameter range between 2.54 to 7.62 cm (1.0 to 3.0 in), which reflects preponderance of residual bark, even though the operator have adjusted the debarker accordingly by settling a more aggressive angle for the cutting tools, while choosing to apply a relatively low pressure on the debarking tools to compensate for fiber loss caused by the more aggressive angle used. However, the observed quality indicator may still be within the acceptable quality indicator range centered to the target value as set by the operator for the log diameter range being processed. For the two following diameter ranges extending respectfully between 7.62 to 8.89 cm (3.0 to 3.5 in) and 8.89 to 10.16 cm (3.5 to 4 in), in consideration of less residual bark on the logs, the operator may have reduced the tool angle toward less aggressive values, while keeping the increase of pressure on the debarking tools, in such a manner that debarking quality indicator observed for these log diameter ranges decreases, while remaining within an acceptable quality indicator range centered to the corresponding target value as set by the operator. For the following log diameter ranges, it can be appreciated that the values of debarking quality indicator increases with log diameter range values, as the operator applies increasing pressure on the debarking tools, in order to maintain the quality indicator value within the acceptable range as set for the diameter range being processed, considering that the tool angle is still adjusted toward less aggressive values.

For the purpose of an alternate texture analysis approach, the detected vertical and horizontal edges may be further processed to obtain texture data as an indication of log surface roughness, by extracting through comparison of the detected edge images, the maximum absolute values to form a single image (ima_rug) representing roughness of the log surface. Such an image can be obtained using the following Matlab™ command:

$$\text{ima\_rug} = \max(|zhe|, |zve|) \quad (6)$$

Figure 19:
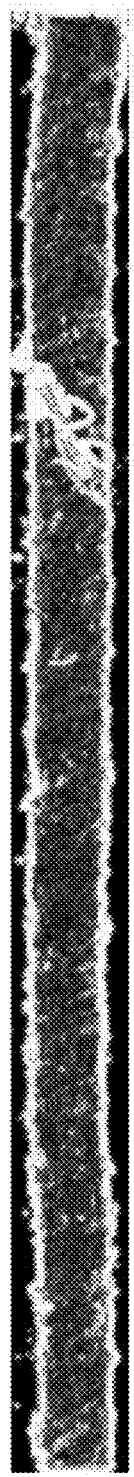
FIG. 19 is an image representing roughness areas on the log surface which can be obtained from the edge detected images of FIGS. 13A and 13B.

A roughness indicative image that can be obtained from the edge detected images or FIGS. 13A and 13B is shown in FIG. 19.

A first series of image analysis tasks according to the present implementation will now be described, whereby the parameters related to the debarking quality of the log surface can be derived from the texture data. In order to provide some immunity to local discontinuity of texture, image analysis is preceded by averaging the texture using a filter of an appropriate dimension (e.g. k=[11,11]) such as provided by the "imfilter" function of Matlab™ according to the following command:

$$\text{Ima\_rug\_}f = \text{imfilter}(\text{ima\_rug}, \text{ones}(k)/(k(1)*k(2))); \quad (7)$$

A first image analysis task aims at identifying the portion of the filtered texture data which can be associated with fiber loss at the surface of the log to generate a corresponding mask (mask_loss) using predetermined thresholds depending upon the relative importance of fiber loss characterizing the surface of the scanned log, the resulting range texture data values as a result of measurement and processing, and the chosen computation mode (floating point or integer). It is to be understood that the thresholds can be readily selected though preliminary measurements with log samples presenting various debarking states, for example in view of predetermined standard quality grades for the debarked logs. In the present implementation, high and low fiber loss minimum threshold have been considered to derive a combined detection, wherein the presence of at least one high pixel value within an area generally characterized by low fiber loss will favor high fiber loss detection, using the "imreconstruct" function of Matlab™ according to the following test:

mask_loss=imreconstruct(mask_high_loss,mask_low-_loss);

wherein:

mask_high_loss=ima_rough_$f$>$T_h$;

mask_low_loss=ima_rough_$f$>$T_l$; (8)

As a result of preliminary measurement with log samples, values of $T_h$=3 and $T_l$=1.5 have been found appropriate.

Moreover, a further roughness threshold has been considered in the generation of a further mask aimed at excluding from fiber loss detection surface areas characterized by relatively smooth log surface such as oxidized or burned areas which can be considered like well debarked wood surface, which surface areas may also include dark areas that could otherwise be mistaken with bark, as will be explained later in more detail. Conveniently, the excluded surface areas are those whose detected roughness value is lower than a predetermined roughness threshold. In the present implementation, a corresponding mask (mask_smooth) may be obtained using an appropriate opening structural element of square dimension (e.g. 11×11) by calling the "imopen" function of Matlab™ according to the following test:

mask_smooth=imopen(ima_rough,strel('square',11))
<0.1&mask_valid; (9)

wherein the outside pixels are excluded from analysis with the use of the predetermined mask_valid mask. In the latter test, ima_rough_f could also be used in replacement of ima_rough. It is to be understood that the exclusion task could be performed later, in a same manner as explained below in the case of fiber loss detection.

Figure 20A:
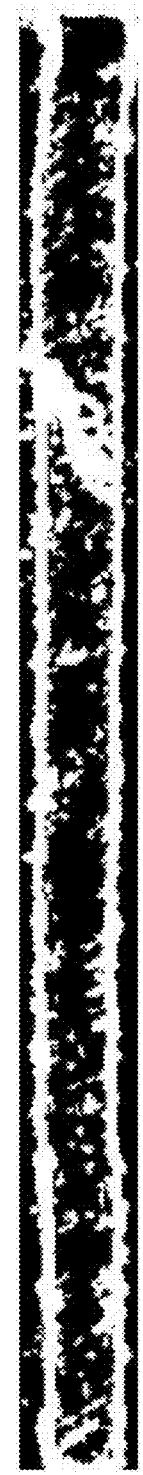
FIGS. 20A and 20B are images respectively representing a mask indicating fiber tear areas and a mask indicating smooth areas of the log surface, as obtained from the roughness indicative image of FIG. 19.
Figure 20B:
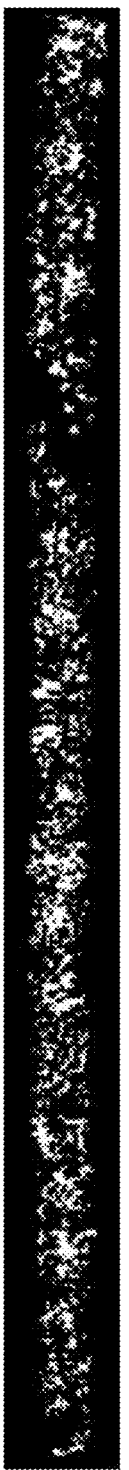

The resulting mask_loss and mask_smooth masks obtained from the roughness indicative image of FIG. 19 are shown in FIGS. 20A and 20B.

As mentioned above, the reflected light intensity image data can be considered through a further analysis, by comparing with a predetermined intensity threshold the reflected light intensity data, to provide a further indication of the residual bark in addition to the resulting quality indicative information based on texture data as described above. For the purpose of this further residual bark detection task, it can be appropriate to first apply a correction to the intensity of image pixels corresponding to the lateral portions of the scanned log, which appear darker as compared with image pixels corresponding to central areas of the log, due to log curvature effect on lighting which is more marked at image edges. A convenient way to perform that correction consists of using a ramp function applying a factor of a first value (e.g. $f_1$=1) to the pixels of the central areas, and a factor of a greater value (e.g. $f_2$=2) to the pixels of the image edges. In the present implementation, a corresponding corrected intensity image (ima_int_c) may be obtained from the scaled intensity image (ima_int) using an appropriate ramp (calibre) in integer 16 bit mode by calling the "uint16" function of Matlab™ according to the following command:

ima_int_$c$=$uint$16(double(ima_int)·*calibre); (10)

The result of this correction task as performed on the scaled intensity image of FIG. 11A which is reproduced in FIG. 21A, can be appreciated by comparison with corrected image shown in FIG. 21B. According to an alternate but more complex approach, it would be possible to obtain a better fitting correction by calculating correction factors specific to each pixel or small pixel area using related angular information that could be derived from profile image data. Then, the further task of residual bark detection aims at identifying the portion of the corrected intensity image data which can be associated with bark at the surface of the log to generate a corresponding mask (mask_bark) using a predetermined threshold, depending upon the wood species involved, the resulting intensity image data values as a result of measurement and processing, and the chosen computation mode (floating point or integer). Here again, it is to be understood that the thresholds can be readily selected though preliminary measurements with log samples presenting various debarking states, for example in view of predetermined standard quality grades for the debarked logs. The corresponding mask (mask_bark) based on the predetermined threshold (thresh_int) may be obtained with appropriate filtering, such as the median filter (medfilt2) along with appropriate opening structural element of square dimension (e.g. 5×5) used in the present implementation by calling the "imopen" function of Matlab™ according to the following test:

mask_bark=imopen
       (ima_int_f<thresh_int&mask_valid,strel
       ('square',5));

wherein:

ima_int_f=medfilt2(ima_int_c,[3,3]);  (11)

and wherein the outside pixels are excluded from analysis with the use of the predetermined mask_valid mask. The result of thresholding as performed on the corrected intensity image of FIG. 21B can be appreciated in the filtered image shown in FIG. 22.

Experiences based on preliminary measurements with log samples presenting various debarking states have shown that fiber loss can be detected with the mask_loss mask on areas surrounding bark zones, where no fiber loss is actually present, due to the surface irregularities characterizing transitions between bark and surrounding, well debarked surface. In order to prevent or at least limit such adverse effect, it is desirable to enlarge to some extent the detected bark zones by appropriate image filtering, such as through the application of structural elements for performing, from the mask_bark mask, closing (imclose), opening (bwareaopen) and dilation (imdilate) operations of appropriate dimension as used in the present implementation by calling from Matlab™ the following command:

mask_bark_enl=imdilate(bark_enl_seed,strel
       ('square',25));

wherein:

bark_enl_seed=bwareaopen(mask_bark_c,40*40);
       and mask_bark_c=imclose(mask_bark,strel('square',15));  (12)

As will be described below in more detail, the obtained mask_bark_enl mask indicating enlarged bark areas can then be subtracted from the mask_loss mask to remove the corresponding detected fiber loss areas, as illustrated with reference to the example of FIGS. 23A to 23C, the enlarged bark areas 94 as indicated by the mask_bark_enl mask of FIG. 23B have been removed from mask_loss mask of FIG. 23A to obtain the corrected image of FIG. 23C showing corresponding corrected areas 94'.

Then, the resulting quality-related parameter data in terms of fiber loss, bark as well as smooth areas obtained from the analysis tasks as described above can be combined on the basis of a given detection priority order, so that any area of the scanned log surface is assigned a single parameter quality information, especially for displaying purpose in the form of a combined image. Conveniently, an identification code from a list of possible codes shown in Table 1 is assigned to the various areas associated with the resulting detection.

TABLE 1

| Parameter/Characteristic | Code |
| --- | --- |
| 1. outside log | 0 |
| 2. well debarked | 1 |
| 3. smooth | 2 |
| 4. bark | 3 |
| 5. fiber loss | 4 |

In the present implementation, smooth areas where neither fiber loss nor bark should be detected are considered first, to assign a corresponding identification code "2", while excluding outside pixels as previously identified (mask_valid) and with an appropriate conversion in integer 8 bit mode, according to the following Matlab™ command:

detect(detect==1&mask_smooth)=2;

wherein:

detect=uint8(mask_valid);  (13)

Then, priority is given to fiber loss detection unless enlarged bark areas are involved, to assign a corresponding identification code "4", according to the following Matlab™ command:

detect(detect==1&~mask_loss &~mask_bark_enl)=4;  (14)

followed by bark code assignment "3" performed according to the following Matlab™ command:

detect(mask_bark_c==1&~mask_smooth)=3  (15)

In the latter command, mask_bark could also be used in replacement of mask_bark_c. Finally, the pixels outside log surface are given the corresponding "0" code on the basis of the binary mask image "mask_valid" referred to above, according to the following Matlab™ command:

detect(~stat_mask)=0  (16)

Figure 24:
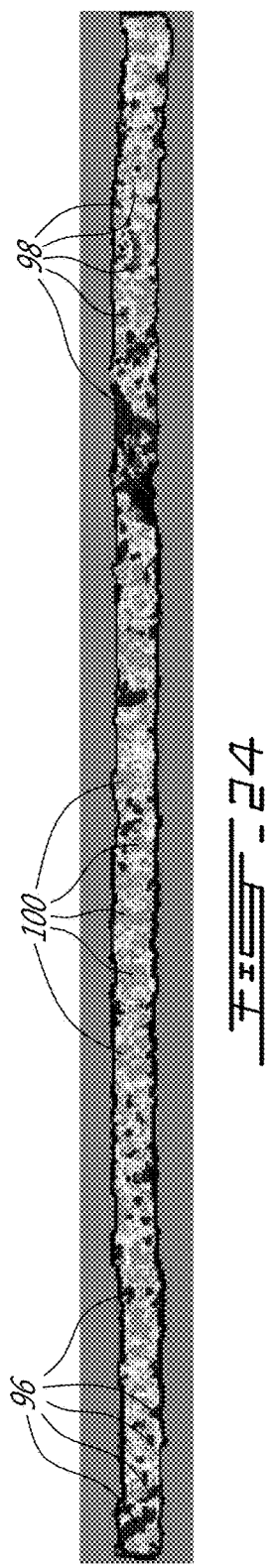
FIG. 24 is a combined image representation of the resulting quality-related parameter data.

An example of resulting quality-related parameter data that have been combined in a single image is given in FIG. 24, wherein fiber loss, bark and smooth areas are indicated at 96, 98 and 100, respectively, for example though different visual texture or colors.

Figure 15:
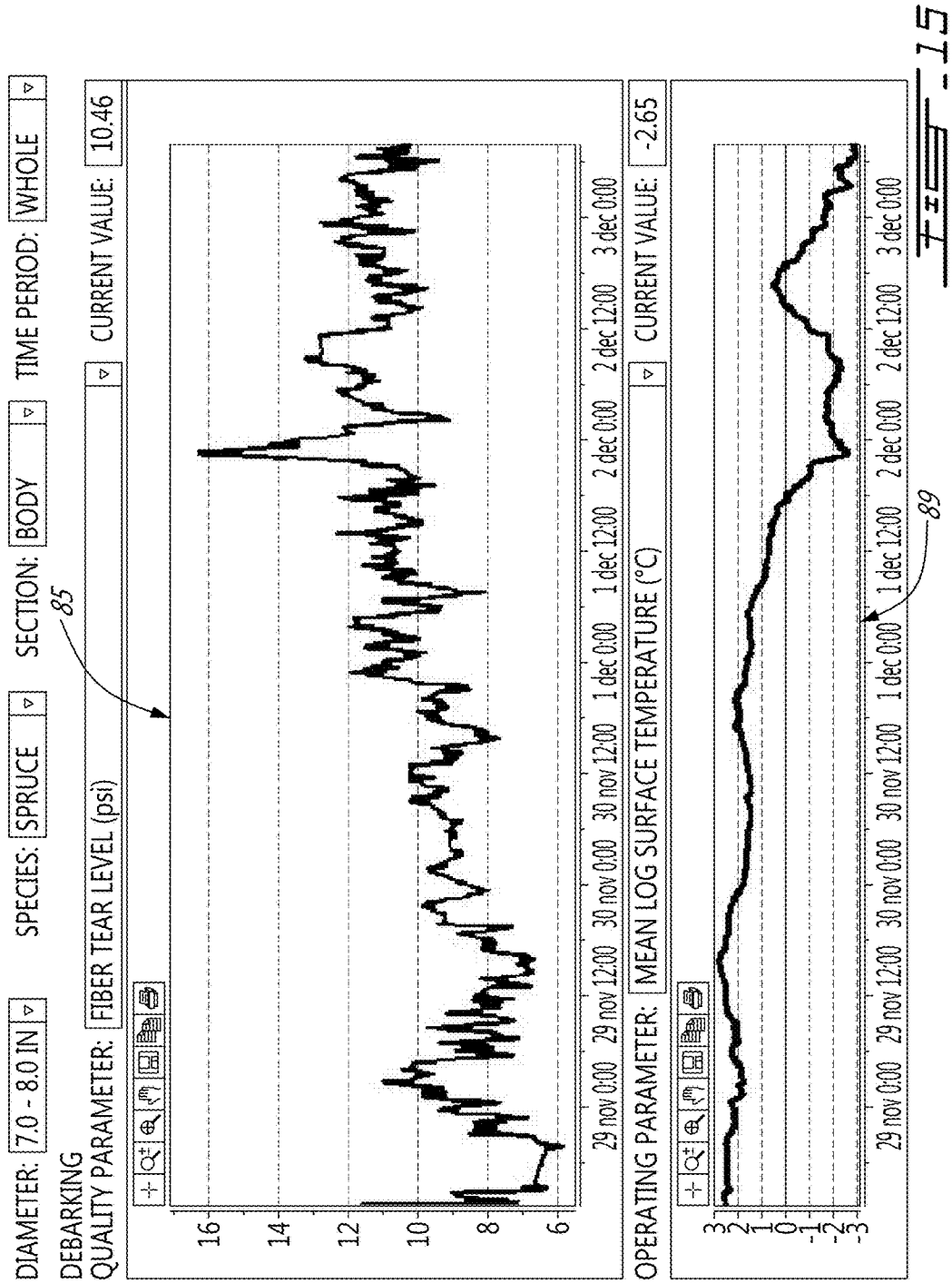
FIG. 15 is a second example of a main screen showing fiber loss level as generated by the computer program.
Figure 16:
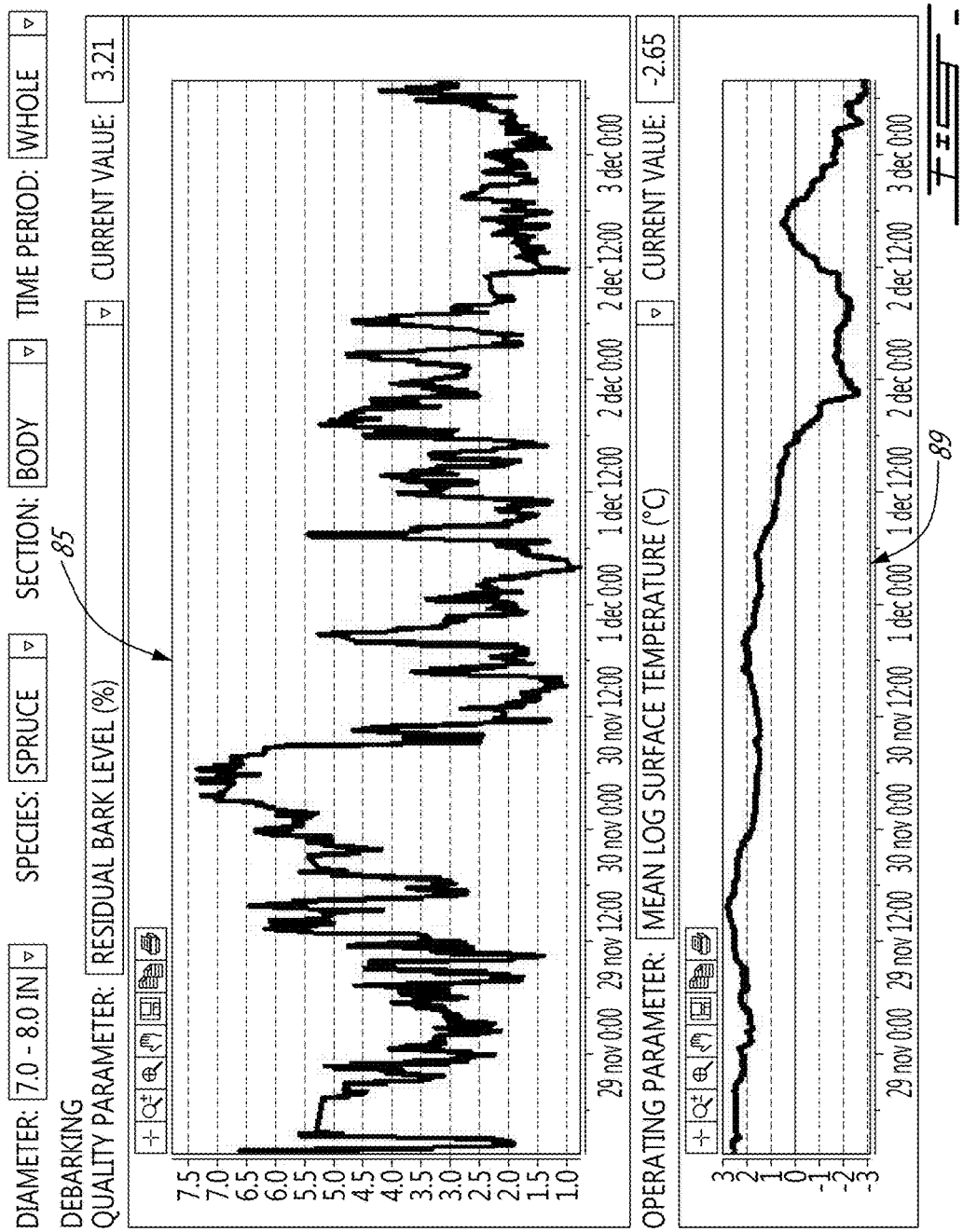
FIG. 16 is a third example of a main screen showing residual bark level as generated by the computer program.
Figure 17:
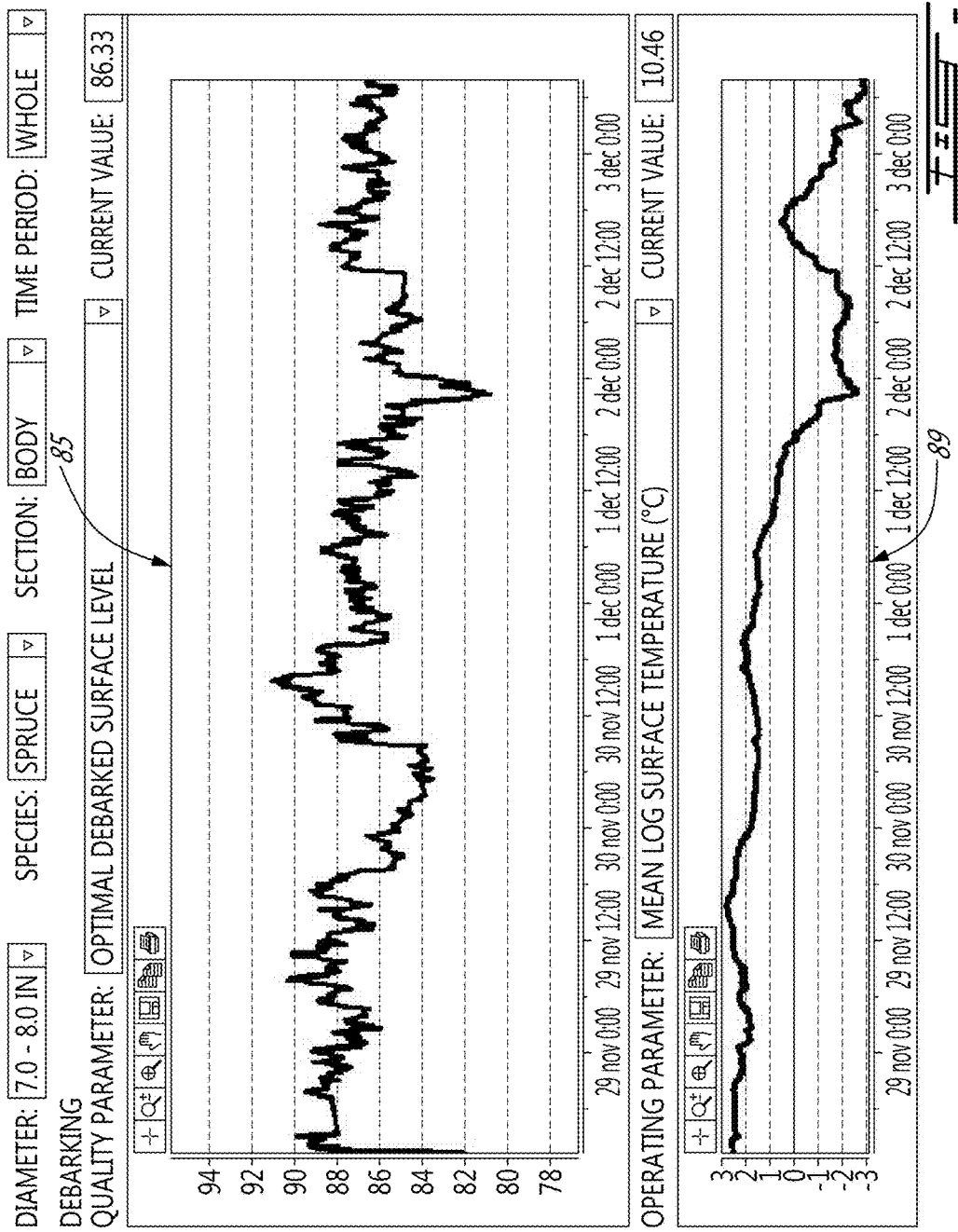
FIG. 17 is a fourth example of a main screen showing residual optimal debarked surface level as generated by the computer program.

Turning back to FIG. 7, the resulting data may be directly viewed by the operator on display 80, in the form of images representing areas of the log surface characterized by the detected parameters, and the operator can enter displaying commands to the detection module through keyboard 81 or any other appropriate data entry means. Optionally, information stored in the database 78 can be read out through link 75 by a control module 79 programmed to allow the operator to have access to historical quality data in the form of report 82, either for each log or for any group of logs corresponding to one or more selected criteria such as diameter range, wood species, scanned log section (leading end, body, trailing end), and trend calculations for a selected period of operation time can be performed by the control module 79. Here again, apart from the option of selecting the log section or sections to be considered for result displaying purposes, the operator may also determine the number of logs (log population, typically between 50 to 300 logs) involved in the calculation of mean values for each quality-related parameter, conveniently based on a moving average relative to the specific time considered. Turning to FIG. 15, there is represented a second example of main screen generated by the computer program, in which the first graph 85 shows evolution of fiber loss level (%) as the selected debarking quality parameter, with respect to the whole period of production time (4 days) as also selected by the operator. According to this second example, the second graph 89 is displayed for presenting evolution of mean log surface temperature as the selected operating parameter, with respect to time. Turning to FIG. 16, there is represented a third example of main screen showing generated by the computer program, in which the first graph 85 shows evolution of residual bark level (%) as the selected debarking quality parameter, with respect to the whole period of production time (4 days) as also selected by the operator. As in the second example, the second graph 89 is displayed for presenting evolution of mean log surface temperature as the selected operating parameter, with respect to time. Turning to FIG. 17, there is represented a fourth example of main screen as generated by the computer program, in which the first graph 85 shows evolution of optimal debarked surface level (%) as the selected debarking quality parameter, with respect to the whole period of production time (4 days) as also selected by the operator. As in the second and third examples, the second graph 89 is displayed for presenting evolution of mean log surface temperature as the selected operating parameter, with respect to time.

Turning back to FIG. 7, warning/alarm signals according to operator's settings can be generated by the control module 79 whenever the value of any quality parameter exceeds preset thresholds. Furthermore, from the controller 67 and through link 70, the detection module 76 may cause the database 78 to automatically store debarker input parameter data including assigned log identification number, log length, selected log debarking diameter range, mean log diameter (unbarked), log surface temperature, as well as debarker operation parameters such as mean pressure applied to the cutting tools, angular position of cutting tools, ring rotational speed and log feed speed, for reporting purposes to the operator. The log identification number being associated with profile image data, texture indicative data, quality parameter data and other information corresponding to each scanned log, it allows the operator to retrieve from the database 78 any desired data related to a specific one or a set of scanned logs, such as fiber loss level, residual bark level and optimal debarked surface level, for whole log or section thereof.

All useful parameters can be made accessible for monitoring and editing by the operator through display 80 and keyboard 81 while the debarking line is in operation, via dialog boxes provided by a proper interface as part of detection module 76. The logs to be inspected can be fed to the detection system 22 in a synchronous mode, so that camera output data related to a predetermined number of scanned logs are stored in the acquisition unit memory until processing of these data by frame grabber 74 is completed. It should be understood that an asynchronous mode of operation could also be applied. Also, the debarking quality data may be used by the control module 79 to assign a quality grade to each debarked log, on the basis of predetermined classification thresholds for the debarking quality parameters that can be established in view of the characteristics of the logs entering the debarker such as diameter, wood species, temperature and moisture content. Furthermore, a marking station (not shown) connected to controller 67 may be provided to apply log identification number and/or quality grade information onto each log.

Optionally, on the basis of input and quality output parameter data, the control module may integrate a mathematical model enabling a real-time optimization of the debarking process, allowing the operator to make fast decisions in view of one or more events such as: debarker failure detection due to mechanical break; premature or misadjustment of a component; resulting effect on debarking quality of a modification or adjustment made to a debarker component related to an operating parameter; detection of raw material variation influencing the debarking quality; or any other change of equipment maintenance monitoring parameter. The mathematical model could be knowledge-based such as an expert system model, fed by the output parameter quality data as generated by detection module, as well as statistical analysis, mathematical modelization and other useful complementary analysis results, which expert system model would establish and apply rules for processing subjective and objective events to make predictive quality assessment and recommend a solution to the operator. Furthermore, the control module 79 optionally makes use of debarking quality information on fiber loss and residual bark as measured to send through link 77 commands enabling the controller 67 to send through link 72 feedback control signals for the required debarker adjustments providing optimal performance in real time. For so doing, in the same manner as explained above, the profile image data is processed to generate data indicative of the surface texture of a debarked log, which data is analyzed to generate resulting data on the debarking quality-related parameters characterizing the debarked surface, i.e. fiber loss and residual bark. Then, the resulting data is used to control the debarking process applied to a further log, by generating control data related to a plurality of input operating parameters of the debarking process, on the basis of predetermined control setpoint data associated with the quality-related parameters. In the example of rotary ring debarker as described above, the input operating parameters may be the mean pressure applied to cutting tools, log feed speed, ring rotational speed, or any combination thereof. A same control strategy adapted to other type of debarker may be implemented by selecting appropriate input operating parameters.

In order to experimentally verify the reliability of debarking quality indicative information provided by the method and system as described above, three trials were performed using a ring debarker operating in a sawmill respectively according to three distinct debarking states characterizing respective samples of processed logs, namely: optimal debarking, with remaining bark, and with fiber loss. Each trial was to check the consistency of the debarking quality-related parameter data resulting from the log surface texture analysis with respect to actual debarking quality that may be appraised through visual inspection by a skilled operator. To avoid any bias due to log diameter variations, the logs of 2.745 m (9 feet) long subjected to the trials were selected from a typical diameter range of 17.8 to 20.3 cm (7 to 8 in), and only data associated to the body section, i.e. central 1.525 m (5 feet), of each debarked log were considered, to avoid debarking quality disturbances due to different cutting tool attack conditions that prevail at log leading and trailing ends. A log population of at least 300 logs of a common species such as black spruce was considered for the calculation (moving average) of mean values for each quality-related parameter.

For each debarking state, a sample of logs was visually inspected by the skilled operator in order to adjust the operation parameters of the ring debarker, especially pressure applied to the cutting tool, according to the desired debarking quality level, while directing a particular attention to distinguish inner bark characterized by pinkish white color, from black spruce sapwood characterized by yellowish color. For the purpose of classification in the first, optimal debarking state, few mils (0.0254 mm) of sapwood fiber loss in rare places on the log body section with a very small level of bark on less than 5-10% of the surface was tolerated. For the purpose of classification in the second state characterized by remaining bark, the pressure on cutting tools were gradually decreased, and the level where a positive pressure adjustment would be required to restore acceptable debarking quality was used a the decision criterion by the classification operator. Roughly, 5-10% of the log body surface covered by inner bark while presenting very small bark spots in rare places, was tolerated. As to the third, fiber loss state of debarking, the pressure on cutting tools were gradually increased in order to eliminate all bark from the log body surface, and the level where a negative pressure adjustment would be required to restore acceptable debarking quality was used a the decision criterion by the classification operator. Then, from the sampled logs, those belonging to the chosen diameter range were identified and subjected to the proposed debarking quality measurement method using the system as described above. Table 2 presents results of the trials in terms of remaining bark and fiber loss according to the three debarking states considered.

TABLE 2

|  |  | DEBARKING STATE | | | NUMBER |
|---|---|---|---|---|---|
|  |  | Remaining bark | Optimal debarking | Fiber loss | OF LOGS INSPECTED |
| Remaining bark (%) | Mean (%) | 16.9 | 6.1 | 1.5 | 640 |
|  | Standard deviation (%) | 14.3 | 7.8 | 2.9 |  |
|  | 1% LSD factor (%) (highly significant) |  | 01.1 |  |  |
|  | 5% LSD factor (%) (significant) |  | 0.9 |  |  |
|  | Standard error | 1 | 0.6 | 0.2 |  |
| Fiber loss (%) | Mean (%) | 4.6 | 5 | 6.1 | 640 |
|  | Standard deviation (%) | 4.3 | 4.9 | 5.3 |  |
|  | 1% LSD factor (%) (highly significant) |  | 0.5 |  |  |
|  | 5% LSD factor (%) (highly significant) |  | 0.4 |  |  |
|  | Standard error | 0.3 | 0.3 | 0.4 |  |

According to the results of the trials, the estimated mean remaining bark was 16.9% for the remaining bark state, 6.1% for the optimal debarking state and 1.5% for the fiber loss state. The estimated mean fiber loss was 4.6% for the remaining bark state, 5% for the optimal debarking state and 6.1% for the fiber loss state. Therefore, the estimated mean remaining bark has varied from 1 to 20%, while the estimated mean fiber loss has varied from 4 to 7%. Table 1 also presents the results of an analysis of variance performed on the data associated with the debarking states, with calculated F values of 8.1 for fiber loss and 334.8 for remaining bark, indicating significant differences between the various trials. In order to identify which trials are different one another, the Least Significant Difference (LSD) was used. For a highly significant trial, LSD is 01.1% for the remaining bark remaining trials, while LSD is 0.9% for a significant trial. The difference between the estimated mean values having largely exceeded 01.1%, the differences between the trials are thus highly significant, and therefore, it is clear that the remaining bark detection is correctly performed. For a highly significant trial, LSD is 0.5% for the fiber loss trials, while LSD is 0.4% for a significant trial. The remaining bark-optimal debarking trial is borderline for being highly significant, whereas the optimal debarking-fiber loss is highly significantly different. A significant difference between the remaining bark-optimal debarking trials was confirmed through visual inspection by the classification operator on a higher number of logs. To observe the difference between the trials and corroborate the results, the standard error was added and subtracted from the estimated mean values to test for overlapping (If an overlap between trials is observed, no difference can be inferred). As observed through LSD analysis, a difference was found between some of the trials, but not for all of them. Therefore, one can conclude that, although the weak difference observed between the remaining bark-optimal debarking trials, there is clearly a significant difference between the trials as a whole, which means that the proposed method is capable of differentiate the fiber loss between the remaining bark and optimal debarking states, and the same method is generally capable of providing a reliable indication of remaining bark and fiber loss in the context of all debarking states considered in the trials. In view of the results of statistical analysis, the proposed method has proved to be useful for detecting the quality of debarking at the surface of wooden logs.

Figure 25:
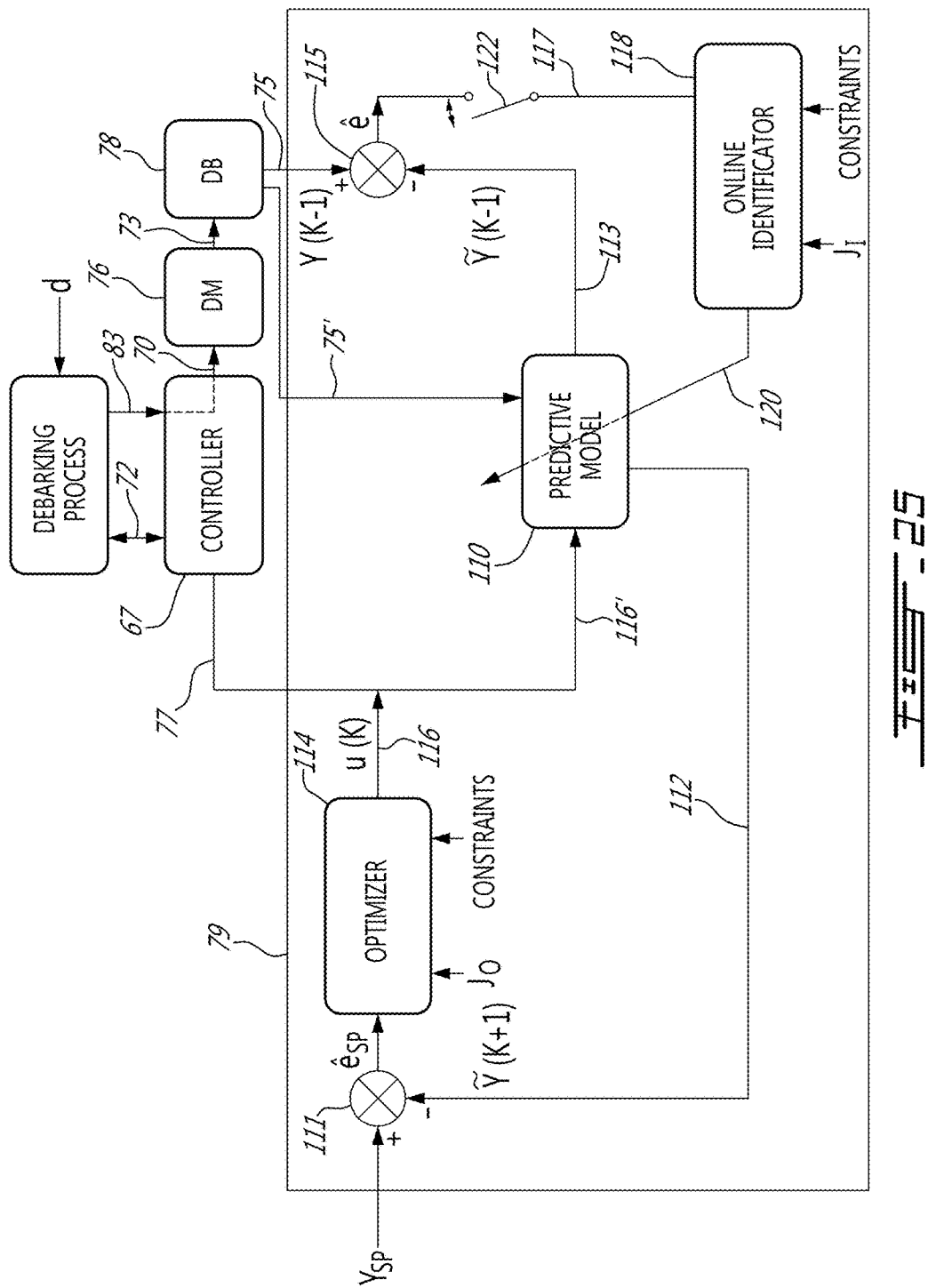
FIG. 25 is a schematic block diagram of a model predictive control (MPC) structure adapted to carry out optimized control of the debarking process.

Referring now to FIG. 25, there is shown a schematic block diagram of a model predictive control (MPC) structure of control module 79 as programmed in the computer, which module 79 is adapted to carry out an optimized control of the debarking process using the proposed strategy. The MPC structure of control module 79 may use a predictive model 110 of the debarking process based on relations involving the input operating parameters (e.g. mean pressure applied to cutting tools, log feed speed, ring rotational speed) and the resulting data on quality-related parameters (i.e. fiber loss and residual bark) for generating, at a first model output 112 shown in FIG. 25, predicted data on the debarking quality-related parameters, which data are represented by the output quality vector $\hat{Y}(k+1)$ associated with the further log to be debarked as designated k+1. The predicted data is then compared at 111 with the control setpoint data $Y_{sp}$ to estimate error data represented by error vector $\hat{e}_{sp}$. The MPC structure of control module 79 further makes use of an optimizer 114 programmed for generating, at optimizer output 116, the control data represented by current control vector u(k) associated with the currently debarked log as designated k, which control data minimize error data $\hat{e}_{sp}$ in accordance with a debarking performance criterion, such as debarking yield maximization, represented as $J_0$ in FIG. 25, and predetermined debarking process constraints imposed on one or more of the refining process input operating parameters. The control data u(k) is fed through link 77 to the controller 67, causing the latter to send through link 72 feedback control signals for the required debarking process adjustments providing optimal performance in real time.

Figure 26:
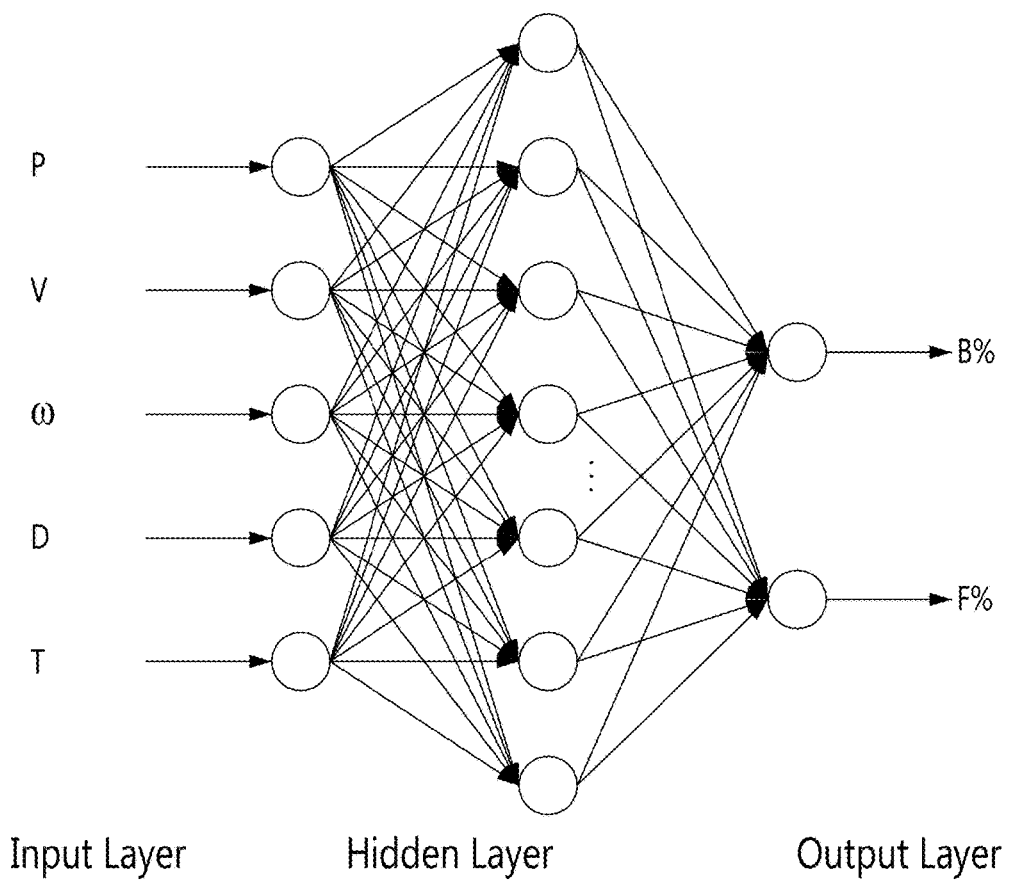
FIG. 26 is an example of predictive model based on a neural network structure.

The control data is concurrently fed via line 116' at an input of the predictive model 110 for updating thereof. According to the example shown in FIG. 25, from the relations on which model 110 is based, the latter is capable of generating at second output 113 thereof an estimation of prior resulting data on the quality-related parameters, which data are represented by the output quality vector $\tilde{Y}(k-1)$ associated with a prior debarked log as designated k−1. The estimation vector $\tilde{Y}(k-1)$ is then compared at 115 with the resulting data Y(k−1) coming via link 75 from database 78 as generated by the detection module 76 in the manner described above in view of FIG. 7, to estimate further error data represented by error vector 6. The predictive model 110 may be built with any appropriate modeling platform such as a neural network, a multivariate linear model, a static gain matrix or a fuzzy logic model. An example of predictive model based on a feed-forward neural network structure is represented in FIG. 26, which model has 1 hidden layer with 12 nodes, 5 operating parameter inputs as defined above (P, V, ω, D, T) and 2 quality-related parameter outputs (F, B) in the example shown. The first step of modeling consisted of performing mill trials to establish a model training file on the basis of the well known design of experiments theory, according to the various debarking operation parameters. Using full factorial designs, 25 tests were performed, involving log dimensional (i.e. log mean diameter D) and temperature measurements before debarking and log inspection after debarking using the three-dimensional profile measuring unit to generate profile image data and reflected light intensity image data from which the quality-related parameters, i.e. fiber loss F (%) and residual bark B (%), were estimated. The model was trained using the fast training function "trainlm" of Matlab™, which function updates weight and bias using the Levenberg-Marquardt back-propagation training algorithm.

Optionally, a plurality of models respectively adapted to a plurality of input parameter ranges may be built, allowing a selection of the most appropriate model according to actual measurements made on logs to be debarked. For example, the predictive model may be selected according to a mean log diameter measurement, from a plurality of models adapted to respective ranges of log diameter. According to an improvement of this approach, for each range of log diameter, there may be a plurality of models further adapted to respective ranges of log surface temperature (e.g. frozen and non-frozen), so that the predictive model may be selected according to a log surface temperature measurement. Another approach would consist of selecting the predictive model according to the log surface temperature measurement only, from a plurality of models adapted to respective ranges of log surface temperature, regardless log diameter.

The predictive model being initially built on actual experimental debarking results, the continuous operation of the debarking process is influenced by disturbances designated by d in FIG. 25, such as cutting tool tip wear, log shape and dimension variations from one log to another, variations of environmental and storage conditions etc., which may cause some model degradation. For this reason, online identification of model may improve its accuracy. For that purpose, the MPC structure of control module 79 further makes use of an online identificator 118 receiving error data ê via line 117 and programmed for adjusting the relations of the predictive model to minimize error data ê, as indicated by output line 120 linked to model 110. Although it may be sufficient to perform the adjustment on an intermittent basis as schematically represented by switching operation 122, a continuous online identification may also be implemented. For a given online identification horizon $H_I$, $n_I$ points are used to minimize the error ê between the model output quality vector $\tilde{Y}(k-1)$ and resulting data Y(k−1) on the quality-related parameters obtained by online measurements, by adjusting the coefficients $K_I$, which are obtained by minimizing the following performance index:

$$J_I = \min_K \sum_{j=1}^{n_I} \hat{e}^2 = \min_K \sum_{j=1}^{n_I} (y - \hat{y})^2 \tag{17}$$

and the constraints on coefficients $K_I$ can be expressed as:

$$\forall_I \in \{1, 2, \ldots m\}, K_I \min < K_I < K_I \max \tag{18}$$

wherein m is the number of coefficients in the model matrix. The Sequential Quadratic Programming (SQP) algorithm can be used for identifying the new coefficients of parameters (variables), as part of a weighting matrix of the model, in order to minimize the error ê. The model coefficients $K_I$ are updated in each horizon of online identification.

According to the present example, the relations of the predictive model further involve at least one log dimensional parameter, such as mean log diameter and/or log taper shape indicator that have been described above with reference to FIGS. 2 and 4A, measured with respect to a further log 10' to be debarked, at la location upstream of the debarker along the log conveying path as shown in FIG. 4A, the measured value being fed to the model 110 through the controller 67 via links 83, 70, 73 and 75' in the example shown in FIG. 25. The proposed MPC structure as described above, involving dimensional measurement before debarking, online quality measurement after debarking as well as control optimization, aims at improving debarked log quality by defining control data related to the chosen input operating parameter (s), in order to comply with the predefined performance criterion, e.g. debarking yield ($D_r$=100−(B+F) %) maximization, while approaching respective setpoints of fiber loss and residual bark on the debarked log surface. In the example of FIG. 25, for a prediction horizon $H_p$ chosen as the time taken for debarking a log, $n_p$ points are considered, and the performance index $J_o$ is defined to find the optimal debarking parameters, P, V and ω which minimize error $\hat{e}_{sp}$, and at the same time to keep a maximum high debarking yield $D_r$:

$$J_O = \max_R D_r + \min_R \sum_{j=1}^{n_P} \hat{e}_{SP}^2 = \max_R D_r + \min_R \sum_{j=1}^{n_P} (y_{SP} - \hat{y})^2 \tag{19}$$

and the constraints on debarking parameters $R_r$ can be expressed as:

$$\forall_r \in \{1, 2, \ldots q\}, R_r \min < R_r < R_r \max \tag{20}$$

wherein q is the number of parameters (variables), the constraints on $R_r$ ensure the optimization results are within available control ranges. Besides the constraints imposed on P, V or ω, the optimization may consider constraints on other parameters such as tool tip path overlap which is a function of V, ω, number of tips and tip width. The optimizer 114 uses the output quality vector $\tilde{Y}(k+1)$ as generated by the model updated through online identification to calculate debarker control data u(k), complying with the performance index $J_O$. Here again, the SQP algorithm can be been used for performing the optimization.

On the basis of actual measurements on logs subjected to debarking at a mill, the performance of debarking in terms of the quality-related parameters as simulated without and with the MPC structure described above, and according to a control sequence based on various states of debarking operating parameters P, V and ω defined in Table 3, is illustrated by the graphs of FIG. 27, for the given control setpoints ($Y_{sp}$) of $B_{SP}$=10.0% and $F_{SP}$=5.0%.

TABLE 3

|   | Phase 1 | Phase 2 | Phase 3 | Phase 4 | Phase 5 |
|---|---|---|---|---|---|
| P | Constant | Varied | Varied | Varied | Varied |
| V | Constant | Const. | Varied | Varied | Varied |
| ω | Constant | Const. | Const. | Varied | Varied |

Figures 27A, 27B:
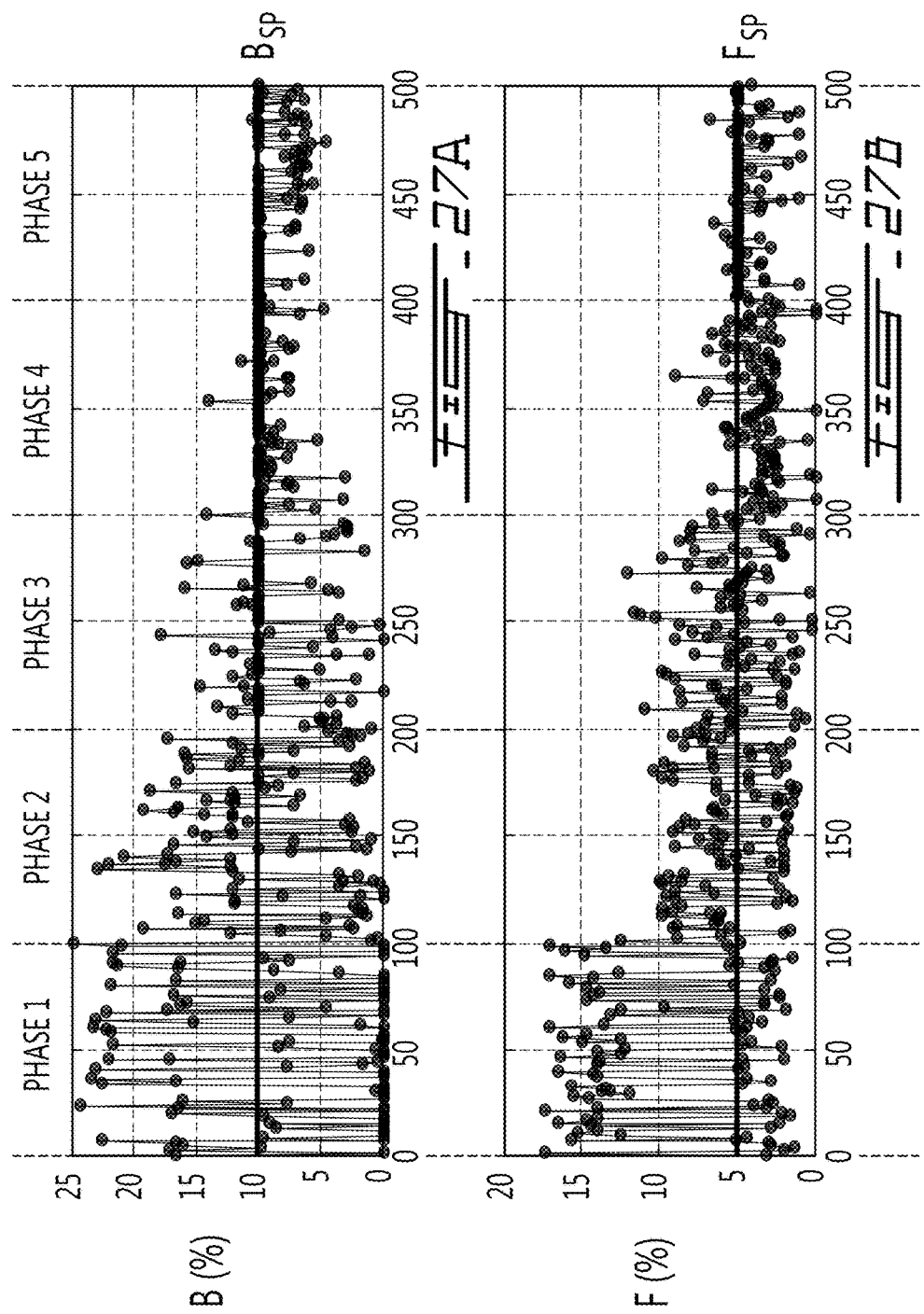
FIG. 27 are graphs showing the performance of debarking in terms of the quality-related parameters as simulated without and with the MPC structure and according to a control sequence based on various states of debarking operating parameters P, V and ω.

Phase 1 involves states of debarking operating parameters which are typical to prior debarking operation at sawmills. The control states are defined according to operator's experience and then generally kept constant, and may sometimes be adjusted according to debarked log qualities that are visible to the operator. As a result of such open loop control, it can be seen from FIGS. 27A and 27B that the estimation of quality-related parameters residual bark B and fiber loss F are far from their respective setpoints. The observed variations of these parameters may be due to changes in log diameter, taper shape and surface temperature characterizing the debarked logs. Phase 2 involves a state of debarking where the control data for the pressure P applied to cutting tools is varied through optimization using the MPC structure, and some performance improvement can be observed when comparing with the performance obtained in phase 1, as shown in FIGS. 27A and 27B, especially regarding fiber loss F. Phase 3 involves a state of debarking where both pressure P and log feed speed V are varied through optimization using the MPC structure, and performance improvement can still be observed when comparing with the performance obtained in phases 1 and 2, as shown in FIGS. 27A and 27B, especially regarding residual bark B. Phase 4 involves a state of debarking where ring rotational speed w is varied in addition to pressure P and log feed speed V through optimization using the MPC structure, and it can be seen from FIGS. 27A and 27B that residual bark B and fiber loss F are closer to their respective setpoints as compared to preceding phases. Phase 5, which still involves variation of pressure P, log feed speed V and ring rotational speed w, further involves subjecting the performance index $J_O$ to a condition of debarking yield maximization. It can be seen from FIG. 27C that the during phases 2 to 5 where the pressure P was varied, the constraints $R_{MIN}$ and $R_{MAX}$ as applied on P was always complied with. Similarly, It can be seen from FIG. 27D that during phases 3 to 5 where the log feed speed V was varied, the constraints $R_{MIN}$ and $R_{MAX}$ as applied on V have always been complied with. Furthermore, It can be seen from FIG. 27E that during phases 4 and 5 where the ring rotational speed ω was varied, the constraints $R_{MIN}$ and $R_{MAX}$ as applied on ω have always been complied with. As to the performance of debarking obtained in terms of the quality-related parameters, it can be appreciated from FIG. 27B in view of FIG. 27A, that the performance index $J_O$ for phases 3 to 5 tends to minimize fiber loss F while complying with the residual bark setpoint $B_{SP}$, the debarking yield being maximized during phase 5. Referring to FIG. 27F, a gradual improvement of debarking quality performance can be observed from the evolution of mean square error MSE through phases 2 to 5.

In order to experimentally verify the performance of the control of a debarking process on the basis of quality indicative information provided by the method and system as described above, further trials were performed using the same ring debarker used in the trials referred to above that confirmed the reliability of the debarking quality indicative information for detection purposes, and the results of the further trials were compared with those obtained using the same ring debarker operating under manual control. For that purposes, a population of more than 5000 logs was processed during a production period shared between the two modes of operation. Remaining bark and fiber loss estimated in terms of mean and standard deviation values were used as reference quality indicators. Table 4 presents results of the trials in terms of remaining bark and fiber loss according to the detection-based control and manual control modes of debarking operation.

TABLE 4

|   |   | DEBARKING OPERATION MODE | | NUMBER OF LOGS INSPECTED |
|---|---|---|---|---|
|   |   | Detection-based | Manual |   |
| Remaining bark (%) | Mean (%) | 5.1 | 3.5 | 1812 |
|   | Standard deviation (%) | 7 | 6 |   |
|   | 1% LSD factor (%) (highly significant) | 0.78 | |   |
|   | 5% LSD factor (%) (significant) | 0.6 | |   |
|   | Standard error | 0.133 | 0.144 |   |
| Fiber loss (%) | Mean (%) | 8.1 | 10.3 | 1812 |
|   | Standard deviation (%) | 4.9 | 5.9 |   |
|   | 1% LSD factor (%) (highly significant) | 0.96 | |   |
|   | 5% LSD factor (%) (highly significant) | 0.73 | |   |
|   | Standard error | 0.09 | 0.11 |   |

Table 4 also presents the results of an analysis of variance performed on the data associated with both debarking operation modes, with calculated F values of 29.5 for fiber loss and 22.8 for remaining bark, indicating significant differences between the various trials. Here again, in order to verify if the trials are different one another, the Least Significant Difference (LSD) was used. For a highly significant trial, LSD is 0.78% for the remaining bark remaining trials, while LSD is 0.6% for a significant trial. The difference between the estimated mean values having largely exceeded 0.78%, the differences between the trials are thus highly significant, and therefore, it is clear that the remaining bark control is correctly performed. For a highly significant trial, LSD is 0.96% for the fiber loss trials, while LSD is 0.73% for a significant trial, thus giving highly significant differences between the trials. Therefore, the control mode of debarking operation has provided a highly significant reduction of fiber loss as compared to the normal operation mode, thus contributing to significantly increase available wood for lumber production. To observe the difference between the trials and corroborate the results, the standard error was added and subtracted from the estimated mean values to test for overlapping (If an overlap between trials is observed, no difference can be inferred). As observed through LSD analysis, a difference was found between all trials. Therefore, one can conclude that there is clearly a significant difference between the trials, thus indicating that the detection-based mode of debarking operation is capable of efficiently controlling the quality debarking parameters in order to limit wood losses and thus improve profitability of the sawmill.

The invention claimed is:

1. A method for detecting the quality of debarking at the surface of a wooden log, comprising the steps of:
   i) measuring a three-dimensional profile of at least a portion of the log surface to generate a corresponding profile image indicating the relative positions of points on said log surface in three-dimensional space;
   ii) processing said profile image to detect edges therein by comparing said relative positions with one another and generate data indicative of the texture of said log surface, said texture data comprising the positions of said detected edges within said profile image; and
   iii) analyzing said texture data to generate resulting data on parameters related to the debarking quality of said log surface, said parameters including fiber loss and residual bark.

2. The debarking quality detecting method of claim 1, further comprising the step of:
   iv) comparing log surface areas respectively characterized by said fiber loss and residual bark with said log surface to estimate fiber loss level and residual bark level.

3. The debarking quality detecting method of claim 2, further comprising before step iv) the step of defining a plurality of surface sections of said log surface including a leading end section, a body section and a trailing end section, wherein said fiber loss level and residual bark level are estimated for one or more of said sections.

4. The debarking quality detecting method of claim 3, wherein said fiber loss level and residual bark level are estimated for at least two of said sections using predetermined weighting factors assigned thereto on the basis of their relative importance in debarking quality detection.

5. The debarking quality detecting method of claim 1, further comprising the step of:
   iv) generating from the resulting data a two-dimensional image representing areas of said log surface respectively characterized by said detected fiber loss and detected residual bark.

6. The debarking quality detecting method of claim 5, wherein said measurement of the three-dimensional profile is performed with respect to a pair of orthogonal reference axis characterized by different resolution levels, said image generating step iv) includes scaling the resulting data to compensate for the resolution difference.

7. The debarking quality detecting method of claim 1, wherein said edges include vertical and horizontal edges of said profile image with respect to a substantially longitudinal axis of said wooden log to obtain said texture data.

8. The debarking quality detecting method of claim 7, wherein said analyzing step iii) includes comparing said detected vertical and horizontal edges as part of said texture data to provide an indication of the ratio of said fiber loss with respect to said residual bark.

9. The debarking quality detecting method of claim 7, wherein said processing step ii) further includes processing said detected vertical and horizontal edges to obtain said texture data as an indication of roughness of said log surface.

10. The debarking quality detecting method of claim 1, wherein said processing step ii) includes flattening said profile image to compensate for the generally curved shape of said log surface.

11. The debarking quality detecting method of claim 10, wherein said profile image flattening is performed by applying thereto a high-pass spatial frequency filter.

12. The debarking quality detecting method of claim 10, wherein said profile image flattening is performed by applying thereto a curve-fitting algorithm.

13. The debarking quality detecting method of claim 9, further comprising the step of:
   iv) measuring light reflection from said log surface portion to generate corresponding reflected light intensity image data; and
   v) comparing with a predetermined intensity threshold the reflected light intensity data to provide a further indication of the residual bark in addition to said resulting data.

14. The debarking quality detecting method of claim 13, wherein said measuring step iv) includes correcting said light intensity image data to compensate for the generally curved shape of said log surface.

15. The debarking quality detecting method of claim 13, further comprising the step of:
   vi) generating from the resulting data a two-dimensional image representing areas of said log surface respectively characterized by said detected fiber loss, said detected residual bark, and a detected roughness value lower than a predetermined roughness threshold.

16. A system for detecting the quality of debarking at the surface of a wooden log, comprising:
   a three-dimensional profile measuring unit for scanning at least a portion of the log surface to generate a corresponding profile image indicating the relative positions of points on said log surface in three-dimensional space;
   data processing means for receiving and processing said profile image to detect edges therein by comparing said relative positions with one another and generate data indicative of the texture of said log surface, said texture data comprising the positions of said detected edges within said profile image; and
   data analyzing means for receiving said texture data to generate resulting data on parameters related to the debarking quality of said log surface, said parameters including fiber loss and residual bark.

17. The debarking quality detecting system of claim 16, wherein said data processing means is for detecting vertical and horizontal edges of said profile image with respect to a substantially longitudinal axis of said wooden log and for processing of said detected vertical and horizontal edges to obtain said texture data as an indication of roughness of said log surface, said system further comprising:
   means for measuring light reflection from said log surface portion to generate corresponding reflected light intensity image data; and
   further data analyzing means for comparing with a predetermined intensity threshold the reflected light intensity data to provide a further indication of the residual bark in addition to said resulting data.

18. A non-transitory software product data recording media in which program code is stored, said program code will cause a computer to perform a method for detecting the quality of debarking at the surface of a wooden log, from a three-dimensional profile image of at least of portion of a surface of said log, said profile image indicating the relative positions of points on said log surface in three-dimensional space, said method comprising the steps of:
   i) processing said profile image to detect edges therein by comparing said relative positions with one another and generate data indicative of the texture of said log surface, said texture data comprising the positions of said detected edges within said profile image; and ii) analyzing said texture data to generate resulting data on parameters related to the debarking quality of said log surface, said parameters including fiber loss and residual bark.

19. The non-transitory software product data recording media of claim 18, wherein said method further comprising the step of:
    iii) comparing log surface areas respectively characterized by said fiber loss and residual bark with said log surface to estimate fiber loss level and residual bark level.

20. The non-transitory software product data recording media of claim 19, wherein said method further comprising before step iii) the step of defining a plurality of surface sections of said log surface including a leading end section, a body section and a trailing end section, wherein said fiber loss level and residual bark level are estimated for one or more of said sections.

21. The non-transitory software product data recording media of claim 20, wherein said fiber loss level and residual bark level are estimated for at least two of said sections using predetermined weighting factors assigned thereto on the basis of their relative importance in debarking quality detection.

22. The non-transitory software product data recording media of claim 18, wherein said method further comprising the step of:
    iii) generating from the resulting data a two-dimensional image representing areas of said log surface respectively characterized by said detected fiber loss and detected residual bark.

23. The non-transitory software product data recording media of claim 22, wherein said three-dimensional profile image is generated by measuring the three-dimensional profile of said log surface with respect to a pair of orthogonal reference axis characterized by different resolution levels, said image generating step iii) includes scaling the resulting data to compensate for the resolution difference.

24. The non-transitory software product data recording media of claim 18, wherein said edges include vertical and horizontal edges of said profile image with respect to a substantially longitudinal axis of said wooden log to obtain said texture data.

25. The non-transitory software product data recording media of claim 24, wherein said analyzing step ii) includes comparing said detected vertical and horizontal edges as part of said texture data to provide an indication of the ratio of said fiber loss with respect to said residual bark.

26. The non-transitory software product data recording media of claim 25, wherein said processing step i) further includes processing said detected vertical and horizontal edges to obtain said texture data as an indication of roughness of said log surface.

27. The non-transitory software product data recording media of claim 18, wherein said processing step i) includes flattening said profile image to compensate for the generally curved shape of said log surface.

28. The non-transitory software product data recording media of claim 27, wherein said profile image flattening is performed by applying thereto a high-pass spatial frequency filter.

29. The non-transitory software product data recording media of claim, 27 wherein said profile image flattening is performed by applying thereto a curve-fitting algorithm.

30. The non-transitory software product data recording media of claim 26, further comprising the step of:
    iii) measuring light reflection from said log surface portion to generate corresponding reflected light intensity image data; and
    iv) comparing with a predetermined intensity threshold the reflected light intensity data to provide a further indication of the residual bark in addition to said resulting data.

31. The non-transitory software product data recording media of claim 30, wherein said measuring step iii) includes correcting said light intensity image data to compensate for the generally curved shape of said log surface.

32. The non-transitory software product data recording media of claim 30, further comprising the step of:
    v) generating from the resulting data a two-dimensional image representing areas of said log surface respectively characterized by said detected fiber loss, said detected residual bark, and a detected roughness value lower than a predetermined roughness threshold.

* * * * *